US010045971B2

(12) United States Patent
Cohen et al.

(10) Patent No.: US 10,045,971 B2
(45) Date of Patent: Aug. 14, 2018

(54) COMPOSITIONS FOR TREATING AMYOTROPHIC LATERAL SCLEROSIS

(71) Applicant: PHARNEXT, Issy les Moulineaux (FR)

(72) Inventors: Daniel Cohen, Saint Cloud (FR); Serguei Nabirochkin, Chatenay-Malabry (FR); Ilya Chumakov, Vaux-le-Penil (FR); Rodolphe Hajj, Saint Germain en Laye (FR)

(73) Assignee: PHARNEXT, Issy les Moulineaux (FR)

( * ) Notice: Subject to any disclaimer, the term of this patent is extended or adjusted under 35 U.S.C. 154(b) by 0 days.

(21) Appl. No.: 15/005,222

(22) Filed: Jan. 25, 2016

(65) Prior Publication Data

US 2016/0136143 A1 May 19, 2016

Related U.S. Application Data

(63) Continuation of application No. 14/473,245, filed on Aug. 29, 2014, now Pat. No. 9,241,933, which is a continuation-in-part of application No. PCT/EP2013/054024, filed on Feb. 28, 2013, which is a continuation-in-part of application No. PCT/EP2012/053565, filed on Mar. 1, 2012, said application No. 14/473,245 is a continuation-in-part of application No. PCT/EP2012/053570, filed on Mar. 1, 2012, and a continuation-in-part of application No. 14/014,650, filed on Aug. 30, 2013, now Pat. No. 9,867,837, which is a continuation-in-part of application No. PCT/EP2012/053565, filed on Mar. 1, 2012, said application No. 14/473,245 is a continuation-in-part of application No. 13/691,981, filed on Dec. 3, 2012, now Pat. No. 8,865,769, which is a continuation of application No. PCT/EP2012/053570, filed on Mar. 1, 2012.

(60) Provisional application No. 61/468,658, filed on Mar. 29, 2011, provisional application No. 61/493,606, filed on Jun. 6, 2011.

(30) Foreign Application Priority Data

Mar. 1, 2011 (EP) .................................. 11305217
Jun. 6, 2011 (EP) .................................. 11305687

(51) Int. Cl.
*A61K 31/42* (2006.01)
*A61K 31/64* (2006.01)
*A61K 31/445* (2006.01)
*A61K 45/06* (2006.01)
*A61K 31/44* (2006.01)
*A61K 31/137* (2006.01)
*A61K 31/138* (2006.01)
*A61K 31/145* (2006.01)
*A61K 31/164* (2006.01)
*A61K 31/185* (2006.01)
*A61K 31/195* (2006.01)
*A61K 31/197* (2006.01)
*A61K 31/428* (2006.01)
*A61K 9/20* (2006.01)

(52) U.S. Cl.
CPC ............ *A61K 31/44* (2013.01); *A61K 31/137* (2013.01); *A61K 31/138* (2013.01); *A61K 31/145* (2013.01); *A61K 31/164* (2013.01); *A61K 31/185* (2013.01); *A61K 31/195* (2013.01); *A61K 31/197* (2013.01); *A61K 31/42* (2013.01); *A61K 31/428* (2013.01); *A61K 31/445* (2013.01); *A61K 31/64* (2013.01); *A61K 45/06* (2013.01); *A61K 9/2004* (2013.01)

(58) Field of Classification Search
CPC .... A61K 2300/00; A61K 31/42; A61K 31/64; A61K 31/445; A61K 45/06
See application file for complete search history.

(56) References Cited

U.S. PATENT DOCUMENTS

| 5,677,344 | A | 10/1997 | Greenfield et al. |
|---|---|---|---|
| 6,391,922 | B1 | 5/2002 | Fogel |
| 8,741,886 | B2 | 6/2014 | Cohen et al. |
| 8,865,769 | B2 | 10/2014 | Cohen et al. |
| 2001/0004640 | A1 | 6/2001 | Inada et al. |
| 2001/0023246 | A1 | 9/2001 | Barritault et al. |
| 2004/0102525 | A1 | 5/2004 | Kozachuk |
| 2006/0276411 | A1 | 12/2006 | Simard et al. |
| 2008/0188510 | A1 | 8/2008 | Yoshino |
| 2009/0069419 | A1 | 3/2009 | Jandeleit et al. |
| 2009/0197958 | A1 | 8/2009 | Sastry et al. |
| 2011/0230659 | A1 | 9/2011 | Tsukamoto et al. |

(Continued)

FOREIGN PATENT DOCUMENTS

| EP | 1 563 846 | 8/2005 |
|---|---|---|
| EP | 1 837 034 | 9/2007 |

(Continued)

OTHER PUBLICATIONS

Cluskey, S. et al. "Mechanisms of neurodegeneration in amyotrophic lateral sclerosis" *Journal of Clinical Pathology: Molecular Pathology*, 2001, pp. 386-392, vol. 54.

(Continued)

*Primary Examiner* — Kendra D Carter
(74) *Attorney, Agent, or Firm* — Browdy and Neimark, PLLC

(57) ABSTRACT

The present invention relates to compositions and methods for the treatment of amyotrophic lateral sclerosis. More specifically, the present invention relates to novel combinatorial therapies for treating amyotrophic lateral sclerosis or a related disorder.

15 Claims, 7 Drawing Sheets

(56) References Cited

U.S. PATENT DOCUMENTS

Figure 1:
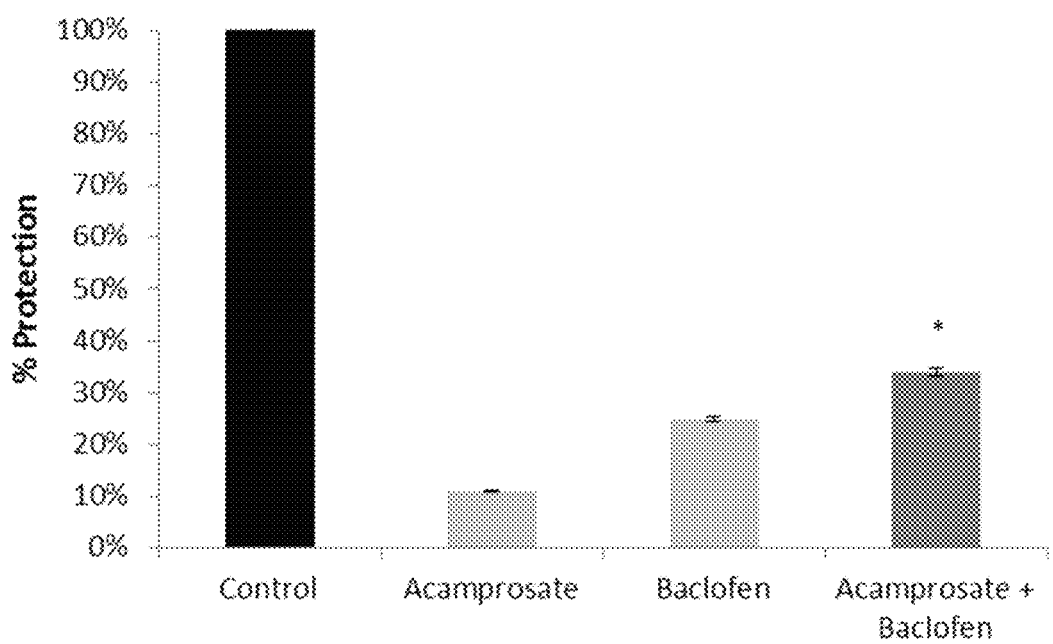

| | | |
|---|---|---|
| 2012/0270836 A1 | 10/2012 | Cohen et al. |
| 2013/0085122 A1 | 4/2013 | Cohen et al. |
| 2013/0090307 A1 | 4/2013 | Cohen et al. |
| 2014/0038927 A1 | 2/2014 | Cohen et al. |
| 2014/0080873 A1 | 3/2014 | Cohen et al. |
| 2014/0371229 A1 | 12/2014 | Cohen et al. |
| 2014/0378440 A1 | 12/2014 | Cohen et al. |

FOREIGN PATENT DOCUMENTS

| | | |
|---|---|---|
| WO | WO 1992/19245 | 11/1992 |
| WO | WO 01/58476 | 8/2001 |
| WO | WO 03/007993 | 1/2003 |
| WO | WO 03/080068 | 10/2003 |
| WO | WO 2007/053596 | 5/2007 |
| WO | WO 2008/006070 | 1/2008 |
| WO | WO 2008/046014 | 4/2008 |
| WO | WO 2008/143361 | 11/2008 |
| WO | WO 2009/000406 | 12/2008 |
| WO | WO 2009/133128 | 11/2009 |
| WO | WO 2009/133141 | 11/2009 |
| WO | WO 2009/133142 | 11/2009 |
| WO | WO 2010/061931 | 6/2010 |
| WO | WO 2010/085352 | 7/2010 |
| WO | WO 2011/054759 | 5/2011 |
| WO | WO 2012/117073 | 9/2012 |
| WO | WO 2012/117075 | 9/2012 |
| WO | WO 2012/117076 | 9/2012 |
| WO | WO 2013/127917 | 9/2013 |
| WO | WO 2013/127918 | 9/2013 |

OTHER PUBLICATIONS

Hama, A. et al. "Synergistic interaction between intrathecal gamma-aminobutyrate (GABA) receptor agonists and an N-methyl-D-aspartate (NMDA) receptor antagonist in rats with neuropathic spinal cord injury pain" *Society for Neuroscience Abstract Viewer and in Itinerary Planner*, 2010, p. 1, vol. 40.

Lyden, P.D. et al. "Combination therapy protects ischemic brain in rats. A glutamate antagonist plus a gamma-aminobutyric acid agonist" *Stroke*, 1994, pp. 189-196, vol. 25.

Costa, C. et al. "Coactivation of $GABA_A$ and $GABA_B$ Receptor Results in Neuroprotection During In Vitro Ischemia" *Stroke*, Jan. 15, 2004, pp. 596-600, vol. 35.

Zhou, C. et al. "Neuroprotection of γ-Aminobutyric Acid Receptor Agonists Via Enhancing Neuronal Nitric Oxide Synthase (Ser847) Phosphorylation Through Increased neuronal Nitric Oxide Synthase and PSD95 Interaction and Inhibited Protein Phosphatase Activity in Cerebral Ischemia" *Journal of Neuroscience Research*, 2008, pp. 2973-2983, vol. 86.

Louzada, P. R. et al. "Taurine prevents the neurotoxicity β-amyloid and glutamate receptor agonists: activation of GABA receptors and possible implications for Alzheimer's disease and other neurological disorders" *The FASEB Journal*, Mar. 2004, vol. 18.

Akan, P. et al. "Pregnenolone protects the PC-12 cell line against amyloid beta peptide toxicity but its sulfate ester does not" *Chemico-Biological Interactions*, 2009, pp. 65-70, vol. 177, No. 1, XP-002613421.

Andrieu, S. et al. "Association of Alzheimer's Disease Onset With Ginkgo Biloba and Other Symptomatic Cognitive Treatments in a Population of Women Aged 75 Years and Older From the EPIDOS Study" *Journal of Gerontology: Medical Sciences*, Apr. 2003, pp. 372-377, vol. 58A, No. 4, XP-009144763.

Aplin, A. C. et al. "Vascular regression and survival are differentially regulated by MT1-MMP and TIMPs in the aortic ring model of angiogenesis" *Am. J. Physiol Cell Physiol*, Aug. 2009, pp. C471-C480, vol. 297, No. 2, XP-002613424.

Dobrek, L. et al. "Future Potential Indications for Pharmacotherapy Using Renin-Angiotensin-Aldosterone System Inhibitory Agents" *Adv. Clin. Exp. Med.*, May 2010, pp. 389-398, vol. 19, No. 3, XP-009144580.

Finsterer, J. et al. "Neurotoxocarosis" *Rev. Inst. Med. Trap. S. Paulo*, pp. 279-287, Sep.-Oct. 2007, vol. 49, No. 5, XP-002623261.

Kakinuma, Y. et al. "Donepezil, an acetylcholinesterase inhibitor against Alzheimer's dementia, promotes angiogenesis in an ischemic hindlimb model" *Journal of Molecular and Cellular Cardiology*, Apr. 2010, pp. 680-693, vol. 48, No. 4, XP-26949580.

Klein, H.E. et al. "Calcium antagonists in dementias. Assessment of the therapeutic efficacy" *Munchener Medizinische Wochenschrift*, 1995, pp. 38, 41-43, vol. 137, No. 47, XP-001525484.

Lee, S.T. et al. "Reduced circulating angiogenic cells in Alzheimer disease" *Neurology*, May 1, 2009, pp. 1858-1863, vol. 72, No. 21, XP-002610857.

Lu, Y. et al. "Neuroprotective activity and evaluation of Hsp90 inhibitors in an immortalized neuronal cell line" *Bioorganic & Medicinal Chemistry*, Feb. 2009, pp. 1709-1715, vol. 17, No. 4, XP-002613422.

Parnetti, L. et al. "Vascular Dementia Italian Sulodexide Study (VA.D.I.S.S.) Clinical and Biological Results" *Thrombosis Research*, pp. 225-233, vol. 87, No. 2.

Polizopoulou, Z. S. et al. "Evaluation of a Proposed Therapeutic Protocol in 12 Dogs with Tentative Degenerative Myelopathy" *Act Veterinaria Hungarica*, pp. 293-301, Sep. 2008, vol. 56, No. 3, XP-009142152.

Pooler, A. M. et al. "The 3-hydroxy-3-methylglutaryl co-enzyme A reductase inhibitor pravastatin enhances neurite outgrowth in hippocampal neurons" *Journal of Neurochemistry*, May 2006, pp. 716-723, vol. 97, No. 3, XP-002571001.

Roehl, A. B. et al. "Neuroprotective properties of levosimendan in an in vitro model of traumatic brain injury" *BMC Neurology*, Oct. 21, 2010, pp. 1-4, vol. 10, No. 1, XP-021074880.

Spuch, C. et al. "Induction of angiogenesis by implantation of encapsulated cells expressing vegf: A new therapy approach on Alzheimer's disease?" *Journal of Neurological Sciences*, Aug. 2009, p. 260, vol. 283, No. 1-2, Issue 1, XP-002571001.

Van Den Bussche, H. et al., "Prescription patterns and effectiveness perception of anti-dementia drugs—A comparison between General Practitioners, Neurologists and Psychiatrists" *Nervenheilkunde*, 2005, pp. 485-492, vol. 24, No. 6, XP-009144765.

Wang, B. et al. "Protective Effects of Wu-Zi-Yan-Zong-Fang on Amyloid β-induced Damage In Vivo and In Vitro" *Database Biosis [Online] Biosciences Information Service*, Aug. 2009, pp. 941-948, vol. 129, No. 8.

Yoshida, K. et al. "Eplerenone Enhances Neovascularization Induced by Endothelial Progenitor Cells in Rat Hindlimb Ischemia" *18th Scientific Meeting of the European-Society-of-Hypertension*, 22nd Scientific Meeting of the Inter, Berlin, Germany, Jun. 14-19, 2008, Poster session PJ-413, XP-009144604, abstract only.

Database Biosis [Online] Bioscience Information Service, Philadelphia, PA, Yoshihiko, K. et al. "Donepezil, an acetylcholiesterase inhibitor against Alzheimer's dementia, promotes angiogenesis in an ischemic limb model of nicotinic alpha 7 k0 mice" Database Accession No. PREV200800197710, Oct. 2007, pp. 1-2, vol. 116, No. 16, Suppl. S., XP-002613420.

Database Biosis [Online] Bioscience Information Service, Philadelphia, PA, Wang, B. et al. "Protective Effects of Wu-Zi-Yan-Zong-Fang on Amyloid β-induced Damage In Vivo and In Vitro" Database Accession No. PREV200900521928, Aug. 2009, pp. 1-2, vol. 129, No. 8, Suppl. S., XP-002613420.

Berenbaum, M.C., "Synergy, additivism and antagonism in immunosuppression: A Critical Review," *Clin. exp. Immunol.*, 1977, pp. 1-18, vol. 28.

Jalbert, J.J. et al., "Dementia of the Alzheimer Type," *Epidemiologic Reviews*, 2008, pp. 15-34, vol. 30.

Jantzen and Robinson, *Modern Pharaceutics 3rd Edition*, published 1996, Marcel Dekker Inc., New York, NY, ed. Gilbert S. Banker et al., p. 596.

Levin, E.D. et al., "Baclofen interactions with nicotine in rats: effects on memory," *Pharmacology, Biochemistry and Behavior*, 2004, pp. 343-348, vol. 79.

Rogers, S.L. et al., "Donepezil Improves Cognition and Global Function in Alzheimer Disease," *Arch Intern Med*, 1998, pp. 1021-1031, vol. 158.

(56) References Cited

OTHER PUBLICATIONS

Rosse, R.B. et al., "Baclofen Treatment in a Patient With Tardive Dystonia," *J. Clin Psychiatry*, 1986, pp. 474-475, vol. 47.

Wilcox, D.M. et al., "Anti-Aβ immunotherapy in Alzheimer's disease; relevance of transgenic mouse studies to clinical trials," *J. Alzheimers Dis.*, 2008, pp. 555-569, vol. 15, No. 4.

Flannery, B. A. et al. "Baclofen for Alcohol Dependence: A Preliminary Open-Label Study" *Alcohol Clin Exp Res.*, Oct. 2004, pp. 1517-1523, vol. 28, No. 10.

Colombo, G. et al. "Role of GABA(B) receptor in alcohol dependence: reducing effect of baclofen on alcohol intake and alcohol motivational properties in rats and amelioration of alcohol withdrawal syndrome and alcohol craving in human alcoholics" *Neurotoxicity Research*, 2004, vol. 6, No. 5, pp. 403-414, abstract No. 0015545024.

Soyka, M, "Efficacy of acamprostate in the relapse prevention of alcohol dependence. Results of clinical trials and therapeutical prospects" *Nervenheilkunde*, 1995, pp. 83-86, vol. 14, No. 2, abstract No. 1995201786.

Lipton, S.A. "Failures and Successes of NMDA Receptor Antagonists: Molecular Basis for the Use of Open-Channel Blockers like Memantine in the Treatment of Acute and Chronic Neurologic Insults" NeuroRx, *The Journal of American Society for Experimental NeuroTherapeutics*, Jan. 2004, pp. 101-110, vol. 1.

Sanger, D.J. et al. "Effects of NMDA receptor antagonists and sigma ligands on the acquisition of conditioned fear in mice" *Psychopharmacology*, 1991, pp. 27-34, vol. 104.

Jentsch, J.D. et al. "A low dose of the alpha$_2$ agonist clonidine ameliorates the visual attention and spatial working memory deficits produced by phencyclidine administration to rats" *Psychopharmacology*, 2004, pp. 76-83, vol. 175.

Olney, J.W. et al. "Pathological Changes Induced in Cerebrocortical Neurons by Phencyclidine and Related Drugs" *Science*, Jun. 16, 1989, pp. 1360-1362, vol. 244, No. 4910.

Davis, S.M. et al. "Selfotel in Acute Ischemic Stroke: Possible Neurotoxic Effects of an NMDA Antagonist" *Stroke*, 2000, pp. 347-354, vol. 31.

Lengyel, C. et al. "Effect of a neuroprotective drug, eliprodil on cardiac repolarisation: importance of the decreased repolarisation reserve in the development of proarrhythmic risk" *British Journal of Pharmacology*, 2004, pp. 152-158, vol. 143.

Schneider, U. et al. "Effects of Acamprosate on Memory in Healthy Young Subjects" *Journal of Studies on Alcohol*, Mar. 1999, pp. 172-175, vol. 60.

Van Der Staay, F.J. et al. "Effects of the cognition impairer MK-801 on learning and memory in mice and rats" *Behavioural Brain Research* 2011, pp. 215-229, vol. 220.

Roberts, M. et al. "NMDA Receptor Antagonists Impair Memory for Nonspatial, Socially Transmitted Food Preference" *Behavioral Neuroscience*, 2002, pp. 1059-1069, vol. 116, No. 6.

Krystal, J.H. "Subanesthetic Effects of the Noncompetitive NMDA Antagonist, Ketamine, in Humans" *Arch. Gen. Psychiatry*, Mar. 1994, pp. 199-214, vol. 51.

Subhan, Z. et al. "Psychopharmacological Effects of Vinpocetine in Normal Healthy Volunteers" *Eur. J. Clin. Pharmacol*, 1985, pp. 567-571, vol. 28.

Thal, L.J. et al. "The Safety and Lack of Efficacy of Vinpocetine in Alzheimer's Disease" *J. Am. Geriatr. Soc.*, Jun. 1989, pp. 515-520, vol. 37, No. 6.

Sandyk, R, et al. "Baclofen-Induced Memory Impairment" *Clinical Neuropharmacology*, 1985, pp. 294-295, vol. 8, No. 3.

Lee, B.Y. et al. "Chronic stimulation of $GABA_A$ receptor with muscimol reduces amyloid β protein (25-35)-induced neurotoxicity in cultured rat cortical cells" *Neuroscience Research*, 2005, pp. 347-356, vol. 52.

Marcade, M. et al. "Etazolate, a neuroprotective drug linking $GABA_A$ receptor pharmacology to amyloid precursor protein processing" *Journal of Neurochemistry*, 2008, pp. 392-404, vol. 106.

Maubach, K. "$GABA_A$ Receptor Subtype Selective Cognition Enhancers" *Current Drug Targets. CNS & Neurological Disorders*, 2003, pp. 233-239, vol. 2.

2014 Alzheimer's disease facts and figures, *Alzheimer's & Dementia*, 2014, pp. e47-e92, vol. 10.

PHRMA, "Researching Alzheimer's Medicines : Setbacks and Stepping Stones" 2012, pp. 1-20.

Maria, B. "Renewed focus on dementia checked by drug challenges" *Chemistry World*, 2014, pp. 1-3.

Chumakov, I. et al. "Combining two repurposed drugs as a promising approach for Alzheimer's disease therapy" *Scientific Reports*, 2015, pp. 1-12, vol. 5.

Scart-Gres, C. et al. "OC30—First Evidence of PXT00864 Effect in the Treatment of Mild AD: Results on 30 Patients From the PLEODIAL I study" *J. Prev. Alz. Dis.*, Summary of Oral Communication at the 7th Conference Clinical Trials on Alzheimer's Disease, 2014, pp. 232-233, vol. 1.

Brasser, S. M. et al. "Alcohol Effects During Acamprosate Treatment: A Dose-Response Study in Humans" *Alcoholism: Clinical and Experimental Research*, Jul. 2004, pp. 1074-1083, vol. 28, No. 7.

Froestl, W. et al. "SGS742: the first $GABA_B$ receptor antagonist in clinical trials" *Biochemical Pharmacology*, 2004, pp. 1479-1487, vol. 68.

Izquierdo, I. et al. "Correlation between the Pharmacology and Long-Term Potentiation and the Pharmacology of Memory" *Neurobiology of Learning and Memory*, 1995, pp. 19-32, vol. 63.

Nakagawa, Y. et al. "The $GABA_B$ receptor antagonist CGP36742 attenuates the baclofen- and scopolamine-induced deficit in Morris water maze task in rats" *Brain Research*, 1997, pp. 101-106, vol. 766.

Tang, A. et al. "Effect of long term baclofen treatment on recognition memory and novelty detection" *Behavioural Brain Research*, 1996, pp. 145-152, vol. 74.

Lu, P. et al. "Silibinin prevents amyloid β peptide-induced memory impairment and oxidative stress in mice" *British journal of Pharmacology*, 2009, pp. 1270-1277, vol. 157.

Carter, M. D. et al. "The Development of New Therapeutics for Alzheimer's Disease" *Clinical Pharmacology & Therapeutics*, Jan. 1, 2010, pp. 475-486, vol. 88, No. 4.

Sawyer, G. T. "Treatment of Multiple Sclerosis with Tolbutamide" *JAMA*, Oct. 1, 1960, pp. 470-473, vol. 174, No. 5.

Yoshitake, I. et al. "First Clinical Application of the DuraHeart Centrifugal Ventricular Assist Device for a Japanese Patient" *Artificial Organs*, Sep. 1, 2009, pp. 763-766, vol. 33, No. 9.

Unger, R. H. et al. "Tolbutamide-Phenformin in Ketoacidosis-Resistant Patients" *JAMA*, Dec. 24, 1960, pp. 2132-2136, vol. 174, No. 17.

Satyanarayana, S. et al. "Pharmacodynamic and Pharmacokinetic Drug Interaction of Mexiletine with Tolbutamide in Rabbits" *Indian Journal of Pharmaceutical Education and Research*, Jan. 1, 2011, pp. 40-45, vol. 45, No. 1.

Wing, L. M. H. et al. "Cotrimoxazole as an inhibitor of oxidative drug metabolism: effects of trimethoprim and sulphamethoxazole separately and combined on tolbutamide disposition" *Br. J. Clin. Pharmac.* Nov. 1, 1985, pp. 482-485, vol. 20, No. 5.

Nistico, R. et al. "The blockade of $K^+$-ATP channels has neuroprotective effects in an in vitro model of brain ischemia" *International Review of Neurobiology*, 2007, pp. 383-395, vol. 82.

Zhao, W. et al. "Identification of Antihypertensive Drugs Which Inhibit Amyloidβ Protein Oligomerization" *Journal of Alzheimer's Disease*, 2009, pp. 49-57, vol. 16, No. 1.

Database WPI, Thomason Scientific, Accession No. 2007-663193, Feb. 11, 2009, XP002661053, pp. 1-10.

Egashira, N. et al. "Mexiletine Reverses Oxaliplatin-Induced Neuropathic Pain in Rats" *J Pharmacol Sci*, Jan. 1, 2010, pp. 473-476, vol. 112, No. 4.

Lee, K. H. et al. "Neuroprotective effects of mexiletine on motor evoked potentials in demyelinated rat spinal cords" *Neuroscience Research*, May 1, 2010, pp. 59-64, vol. 67, No. 1.

Ates, O. et al. "Neuroprotective effect of mexiletine in the central nervous system of diabetic rats" *Molecular and Cellular Biochemistry*, Mar. 16, 2006, pp. 125-131, vol. 286, No. 1-2.

(56) References Cited

OTHER PUBLICATIONS

Hewitt, K. E. et al. "The use-dependent sodium channel blocker mexiletine is neuroprotective against global ischemic injury" *Brain Research*, Apr. 20, 2001, pp. 281-287, vol. 898, No. 2.

Kaptanoglu, E. et al. "Mexiletine treatment-induced inhibition of caspase-3 activation and improvement of behavioral recovery after spinal cord injury" *J Neurosurg: Spine*, Jul. 1, 2005, pp. 53-56, vol. 3.

Nishiyama, K. et al. "Mexiletine for Painful Alcoholic Neuropathy" *Internal Medicine*, Jun. 1, 1995, pp. 577-579, vol. 34, No. 6.

Kapural, L. et al. "Intrathecal Ziconotide for Complex Regional Pain Syndrome: Seven Case Reports" *Pain Practice*, Jun. 4, 2009, pp. 296-303, vol. 9, No. 4.

Tuttolomondo, A. et al. "Neuron Protection as a Therapeutic Target in Acute Ischemic Stroke" *Current Topics in Medicinal Chemistry*, Oct. 2009, pp. 1317-1334, vol. 9, No. 14.

O'Collins, V. E. et al. "Evaluation of combination therapy in animal models of cerebral ischemic" *Journal of Cerebral Blood Flow & Metabolism*, Feb. 1, 2012, pp. 585-597, vol. 32, No. 4.

Baudelet, C. et al. "Evidence for a Neuroprotective Effect of Pyrid-3-yl-sulphonyl-urea in Photochemically Induced Focal Ischaemia in Rats: Magnetic Resonance Imaging Evaluation" *J. Pharm. Pharmacol.*, Aug. 8, 1999, pp. 967-960, vol. 51, No. 8.

Nagai, H. et al. "The effect of a novel loop diuretic, torasemide, on ischemic cerebral edema in Mongolian gerbils" *Japanese Journal of Pharmacology*, Jan. 1, 1992, p. 289P, vol. 59, No. Suppl. 1, abstract P-130.

Staub, F. et al. "Swelling of glial cells in lactacidosis and by glutamate: significance of Cl-transport" *Brain Research*, Apr. 30, 1993, pp. 69-74, vol. 610, No. 1.

Westermaier, T. et al. "The authors reply" *Critical Care Medicine*, Oct. 1, 2010, pp. 2084-2085, vol. 38, No. 10.

Written Opinion in International Application No. PCT/EP20121053568, dated Sep. 10, 2012, pp. 1-13.

Lal, R. et al. "Arbaclofen Placarbil, a Novel R-Baclofen Prodrug: Improved Absorption, Distribution, Metabolism, and Elimination Properties Compared with R-Baclofen" *The Journal of Pharmacology and Experimental Therapeutics*, 2009, pp. 911-921, vol. 330, No. 3.

Hanafi, R. et al. "Baclofen ester and carbamate prodrug candidates: A simultaneous chromatographic assay, resolution optimized with DryLab" *Journal of Pharmaceutical and Biomedical Analysis*, 2011, pp. 569-576, vol. 56.

Wishart, D. S. et al. "DrugBank: a knowledge for drugs, drug actions and drug targets" *Nucleic Acids Research*, 2008, pp. D901-D906, vol. 36.

Xu, F. et al. "Discovery of a novel potent $GABA_B$ receptor agonist" *Bioorganic & Medicinal Chemistry Letters*, 2011, pp. 6582-6585, vol. 21.

Ettmayer, P. et al. "Lessons Learned from Marketed and Investigational Prodrugs" *Journal of Medicinal Chemistry*, May 6, 2004, pp. 2393-2404, vol. 47, No. 10.

Lacomblez, L. et al. "Dose-Ranging Study of Riluzole in Amyotrophic Lateral Sclerosis" *Lancet*, pp. 1425-1431, vol. 347.

Samii, A. et al. "Parkinson's Disease" *Lancet*, 2004, pp. 1783-1793, vol. 363.

Savitt, J. M. et al. "Diagnosis and treatment of Parkinson disease: molecules to medicine" *The Journal of Clinical Investigation*, Jul. 2006, pp. 1744-1754, vol. 116, No. 7.

Abbott, A. "Levodopa: the story so far" *Nature*, Aug. 26, 2010, pp. S6-S7, vol. 466.

Singer, C. A. et al. "The Mitogen-Activated Protein Kinase Pathway Mediates Estrogen Neuroprotection after Glutamate Toxicity in Primary Cortical Neurons" *The Journal of Neuroscience*, Apr. 1, 1999, pp. 2455-2463, vol. 19, No. 7.

Dauer, W. et al. "Parkinson's Disease: Mechanisms and Models" *Neuron*, Sep. 11, 2003, pp. 889-909, vol. 39.

Chiò, A. et al. "Prognostic factors in ALS: A critical review" *Amyotrophic Lateral Sclerosis*, 2009, pp. 310-323, vol. 10.

COMPOSITIONS FOR TREATING AMYOTROPHIC LATERAL SCLEROSIS

CROSS-REFERENCE TO RELATED APPLICATIONS

This application is a continuation of Ser. No. 14/473,245, filed Aug. 29, 2014, now U.S. Pat. No. 9,241,933, which is a continuation-in-part of PCT/EP2013/054024, filed Feb. 28, 2013, which is a continuation-in-part of PCT/EP2012/053565, filed Mar. 1, 2012, which claims the benefit of Ser. No. 61/468,658, filed Mar. 29, 2011; and is a continuation-in-part of PCT/EP2012/053570, filed Mar. 1, 2012, which claims the benefit of Ser. No. 61/468,658, filed Mar. 29, 2011 and 61/493,606, filed Jun. 6, 2011, the disclosures of which are hereby incorporated by reference in their entirety, including all figures, tables and amino acid or nucleic acid sequences.

This application is a continuation-in-part of Ser. No. 14/014,650, filed Aug. 30, 2013, which is a continuation-in-part of International Application No. PCT/EP2012/053565, filed Mar. 1, 2012, which claims the benefit of U.S. Provisional Application Ser. No. 61/468,658, filed Mar. 29, 2011, the disclosures of which are hereby incorporated by reference in their entirety, including all figures, tables and amino acid or nucleic acid sequences.

This application is a continuation-in-part of Ser. No. 13/691,981, filed Dec. 3, 2012, which is a continuation of PCT/EP2012/053570, Mar. 1, 2012, which claims the benefit of U.S. Provisional Patent Application Nos. 61/468,658, filed Mar. 29, 2011 and 61/493,606, filed Jun. 6, 2011, the disclosures of which are hereby incorporated by reference in their entirety, including all figures, tables and amino acid or nucleic acid sequences.

FIELD OF THE INVENTION

The present invention relates to compositions and methods for treating amyotrophic lateral sclerosis and related disorders. More specifically, the present invention relates to novel combinatorial therapies for the treatment of amyotrophic lateral sclerosis and related disorders.

BACKGROUND OF THE INVENTION

Amyotrophic lateral sclerosis (ALS), also known as Lou Gehrig's disease, is the most frequent adult motor neuron disease. It was first described in 1869 by the French neurologist Jean-Martin Charcot. This disease is characterized by degeneration and death of motor neurons, which leads to generalized weakness and muscle atrophy. The course of the disorder is inexorably progressive, with 50% of patients dying within 3 years of onset. ALS appears as a rare disease with a prevalence of 4-6 per 100 000 each year and an incidence of 1-2 per 100 000 each year.

Most cases (90%) are classified as sporadic ALS (SALS), and the remainder 10% are inherited and referred to as familial ALS (FALS), with a Mendelian pattern of inheritance. From a clinical standpoint, familial (FALS) and sporadic (SALS) cases cannot be distinguished from one another, apart from a mean age at onset for SALS that is 10 years later than for FALS (56 years versus 46 years) [1]. The causes for most cases of ALS are unknown and the clinical course is highly variable, suggesting that multiple factors underlie the disease mechanism. Few treatments are available.

The hallmark of this disease is the selective death of motor neurons located in the brainstem, motor cortex and spinal cord leading to paralysis of voluntary muscles. The paralysis begins focally and disseminates in a pattern that suggests that degeneration is spreading among contiguous pools of motor neurons. Mortality normally results when control of the diaphragm is impaired and the ability to breathe is lost.

ALS is characterized by progressive manifestations of dysfunction of both lower and upper motor neurons. Lower motor neurons connect the brainstem and spinal cord to muscle fibres. Their dysfunction leads to muscle atrophy, cramps and fasciculations (small, local, involuntary muscle contraction). Upper motor neurons originate in motor region of the cerebral cortex or the brainstem and carry motor information down to motor neurons that are directly responsible for stimulating the target muscle. Their dysfunction leads to spasticity (continuous muscle contraction that interfere with gait, movement, and speech) and pathological reflexes [2]. The other related motor neuron diseases are usually distinguished by the type of nerve cells impaired, i.e. upper or lower motor neurons: they are known as primary lateral sclerosis (PLS), progressive muscular atrophy (PMA), pseudobulbar palsy and progressive bulbar palsy (PBP).

Diagnosis of ALS is based on clinical signs, established by neurologist on the basis of history, topographic distribution of the neuronal loss and the finding of some characteristic cytological changes. However, there is no clear-cut diagnostic test of ALS available. Clinical features are classified in accordance with affected neurological regions that are bulbar, cervical, and lumbar.

As already mentioned, degeneration in ALS predominantly affects the motor system. However, cognitive and behavioral, as well as sensory symptoms have recently been reported [3,4] and there is evidence for overlap between frontotemporal dementia (FTD) and ALS both clinically and pathologically [5].

Some weak evidences suggest that ALS onset can be triggered by putative environmental factors [6,7].

Several mutated genes or genomic regions have been reported to cause or predispose to ALS as well as to ALS with FTD [8-10]. For instance, about 20-25% of all FALS cases and around 1% of SALS cases arise because of mutations in superoxide dismutase SOD1 [11]. Multiple clinical presentations within the same family are obtained with the same SOD1 mutation which does not necessarily cause a homogenous phenotype. There is no clear correlation between enzyme activity, clinical progression and disease phenotype. However, the period of the disease is similar whatever the mutation is. Historically, the discovery of SOD1 mutations led to the generation of the first animal models of ALS. They develop a motor neuron disease closely resembling human ALS [12,13]. Among other genes implicated in development of ALS or related motor neuron diseases, alsin, an exchange factor for Rab5A [14], senataxin, potentially involved in RNA processing, VAPB protein regulating vesicle transport, the major axonal retrograde motor protein dynactin, mitochondrial genes for cytochrome c oxidase and isoleucine tRNA synthetase [15,16], angiogenic modulators VEGF and angiogenin [17], can be mentioned.

ALS is a complex disease with multiple causes and the precise mechanisms involved in the pathogenesis of this disease are not yet resolved. This challenges the discovery of effective pharmacologic therapies. Clinical trials had shown that survival, but not function, is modestly prolonged by riluzole in ALS [18]. Nevertheless, riluzole is currently the only drug approved and the only known therapy for ALS. Regarding to the severity of disease, it is consequently administered as a disease-modifying compound to all the patients suffering from ALS.

WO 2009/133128, WO 2009/133141, WO 2009/133142, WO 2011/054759, WO 2009/068668 and WO 2009/153291 disclose potential treatments for several neurodegenerative diseases, among which ALS.

First attempts at establishing guidelines for non-pharmacological therapies were performed. However, standards are still based on expert opinion and differ between countries.

Accordingly, there is still a strong need in the art for novel and effective therapies for treating ALS.

SUMMARY OF INVENTION

The present invention provides novel compositions and methods for treating ALS and related disorders. The invention stems, inter alia, from the identification of drug combinations which provide improved therapeutic effect and clinical benefit to subjects having ALS.

More particularly, an object of the invention relates to a composition for use in the treatment of ALS or a related disorder, comprising at least two drugs selected from acamprosate, baclofen, cinacalcet, mexiletine, sulfisoxazole and torasemide, or a salt, prodrug, derivative of any chemical purity, or sustained-release formulation thereof.

A further object of the invention is a method for treating ALS or a related disorder in a subject in need thereof, comprising administering to the subject at least two drugs selected from acamprosate, baclofen, cinacalcet, mexiletine, sulfisoxazole and torasemide, or a salt, prodrug, derivative of any chemical purity, or sustained-release formulation thereof.

Preferred examples of drug combinations for use in the invention include, e.g., baclofen and acamprosate; acamprosate and cinacalcet; torasemide and baclofen; baclofen and cinacalcet; torasemide and sulfisoxazole; mexiletine and cinacalcet; or baclofen and acamprosate and torasemide.

In a particular embodiment of the invention, the composition further comprises riluzole, or a salt, prodrug, derivative of any chemical purity, or sustained-release formulation thereof.

The compositions in the invention may further comprise one or several pharmaceutically acceptable carrier(s) or excipient(s), and they may be administered repeatedly to the subject. Preferred compositions are administered orally. Moreover, the drugs may be formulated or administered together, separately or sequentially.

The invention is suitable for treating ALS in any mammalian subject, particularly in a human subject, at any stage of the disease. The invention may be used to retard the development of the disease, to reduce, delay or prevent paralysis, motor neuron degeneration and/or pain, and/or to increase survival.

LEGEND TO THE FIGURES

FIG. 1: Effect of baclofen and acamprosate combination therapy against glutamate toxicity on neuronal cortical cells. Glutamate intoxication is significantly prevented by the combination of baclofen (400 nM) and acamprosate (1.6 nM) whereas, at those concentrations, baclofen and acamprosate alone have no significant effect on intoxication. *: $p<0.001$, significantly different from glutamate intoxication; (ANOVA+Dunnett Post-Hoc test).

Figure 2A:
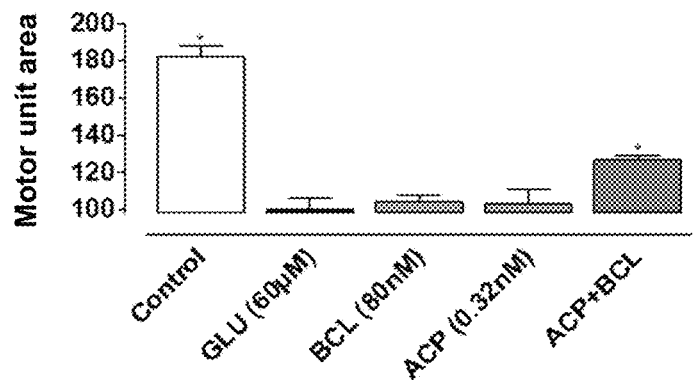
Figure 2B:
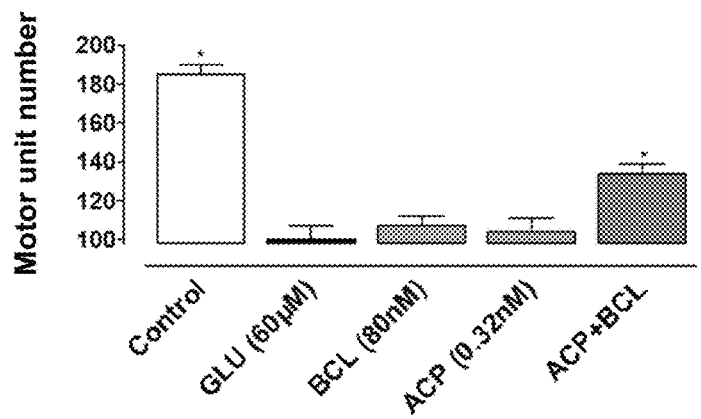
Figure 2C:
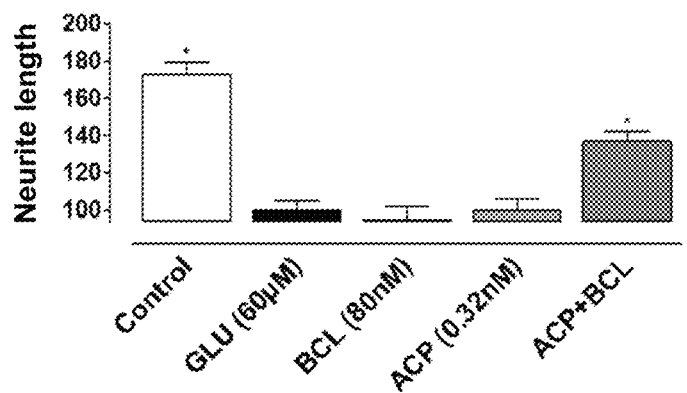

FIGS. 2 A-C: Effect of baclofen and acamprosate combination therapy against glutamate (GLU) toxicity in the nerve-muscle cells co-culture model, on number (A), area (B), and neurite length (C) of motor units. Whatever the endpoint considered, glutamate intoxication is significantly prevented by the combination of baclofen (BCL, 80 nM) and acamprosate (ACP, 0.32 nM), whereas, at those concentrations, baclofen and acamprosate alone have no significant effect on intoxication. *: $p<0.05$, significantly different from glutamate intoxication; (ANOVA+Dunnett Post-Hoc test).

Figure 3:
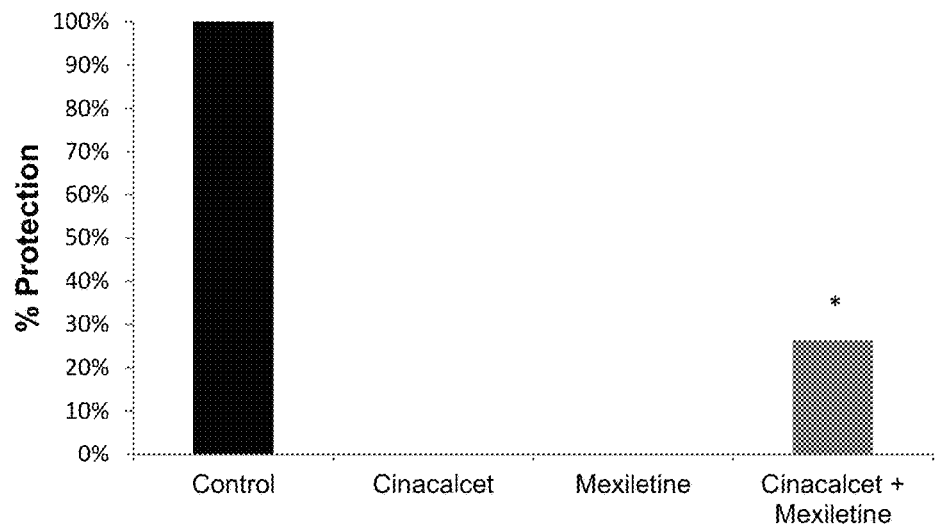

FIG. 3: Effect of cinacalcet and mexiletine combination therapy against glutamate toxicity on neuronal cortical cells. The glutamate intoxication is significantly prevented by the combination of cinacalcet (64 pM) and mexiletine (25.6 pM) whereas, at those concentrations, cinacalcet and mexiletine alone have no significant effect on intoxication. *: $p<0.001$, significantly different from glutamate intoxication; (ANOVA+Dunnett Post-Hoc test).

Figure 4:
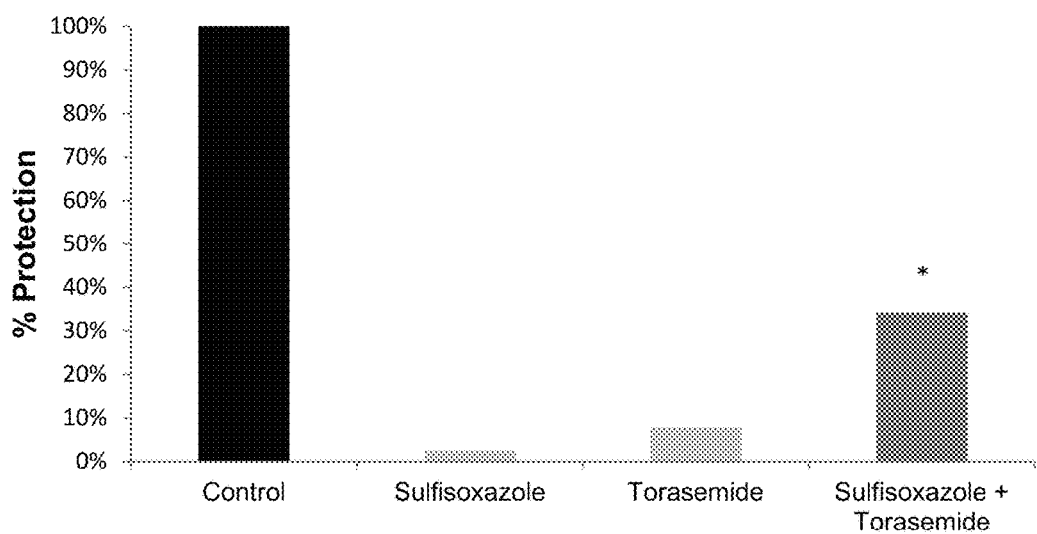

FIG. 4: Effect of sulfisoxazole and torasemide combination therapy against glutamate toxicity on neuronal cortical cells. The glutamate intoxication is significantly prevented by the combination of sulfisoxazole (6.8 nM) and torasemide (400 nM) whereas, at those concentrations, sulfisoxazole and torasemide alone have no significant effect on intoxication. *: $p<0.001$, significantly different from glutamate intoxication; (ANOVA+Dunnett Post-Hoc test).

Figure 5A:
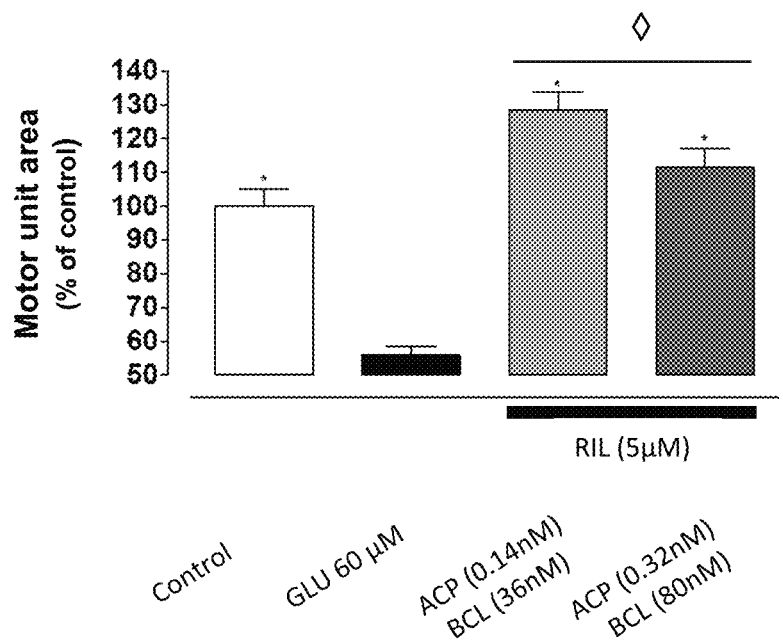
Figure 5B:
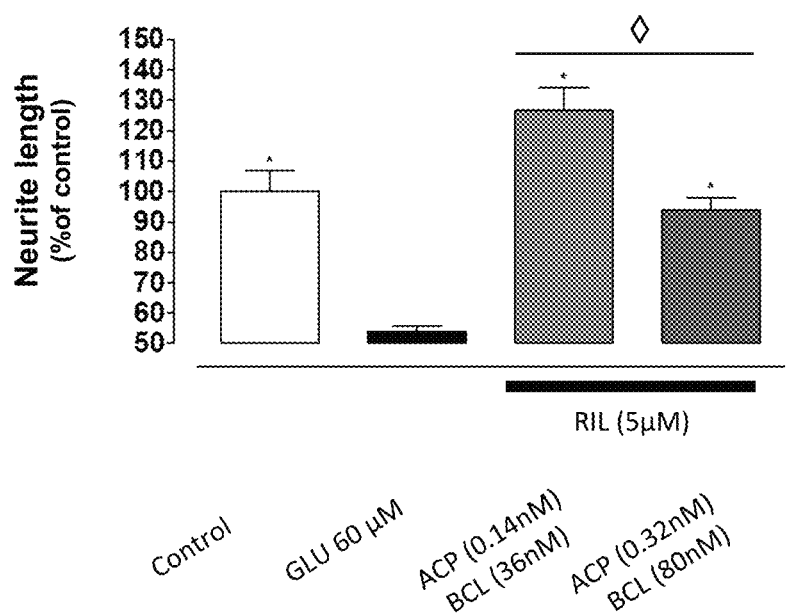

FIGS. 5 A-B: Baclofen (BCL) and acamprosate (ACP) combination acts as an enhancer of riluzole (ML) protecting effect against glutamate toxicity, in the nerve-muscle cells co-culture model, area (A), and neurite length (B) of motor units. A significantly stronger enhancing effect is observed when using concentrations as low as ACP (0.14 nM) BCL (36 nM), when compared to the effect obtained for ACP (0.32 nM) BCL (80 nM). (*: $p<0.001$, significantly different from glutamate intoxication; ◊: $p<0.001$, significantly different (ANOVA+Dunnett Post-Hoc test)).

Figure 6A:
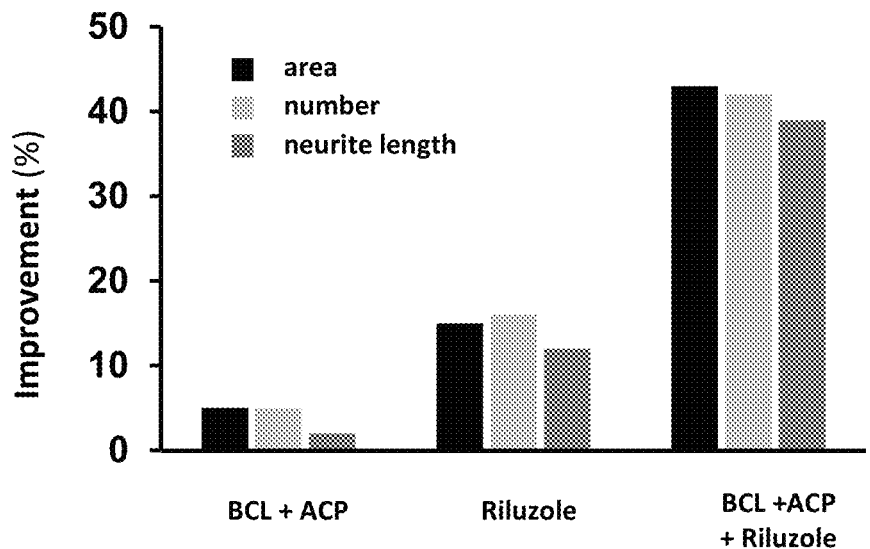
Figure 6B:
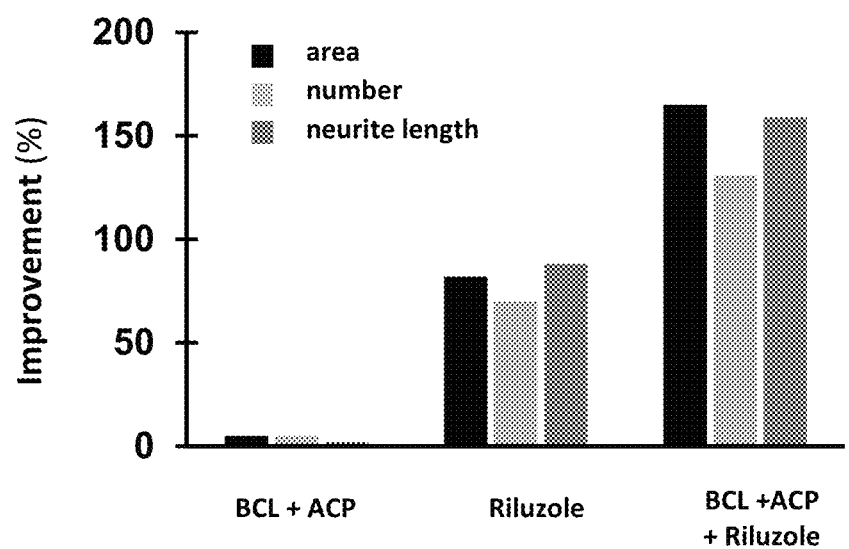

FIGS. 6 A-B: Baclofen (BCL) and acamprosate (ACP) act synergistically with riluzole in protecting neuromuscular junctions against glutamate toxicity in the nerve-muscle cells co-culture model. An important improvement of protection is observed when measuring the number, area, as well as neurite length of motor units. A) an improvement of endpoints from 2 to 5% is observed for ACP (0.14 nM) BCL (36 nM) mix; from 12 to 16% when using riluzole (0.04 μM) alone; whereas the combination of the 3 drugs results in an improvement from 39 to 43%. B) an improvement of endpoints from 2 to 5% is observed for ACP (0.14 nM) BCL (36 nM) mix; from 70 to 88% when using riluzole 5 μM; whereas the combination of the 3 drugs results in an improvement from 131 to 165%. (*: $p<0.001$, significantly different from glutamate intoxication; ◊: $p<0.001$, significantly different (ANOVA+Dunnett Post-Hoc test)).

Figure 7A:
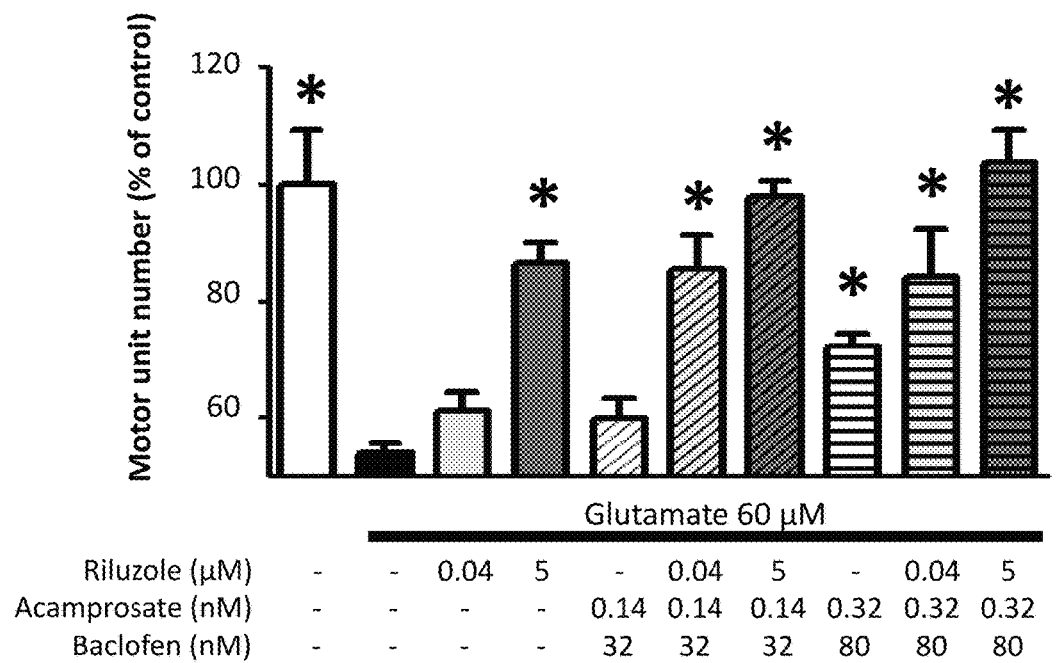
Figure 7B:
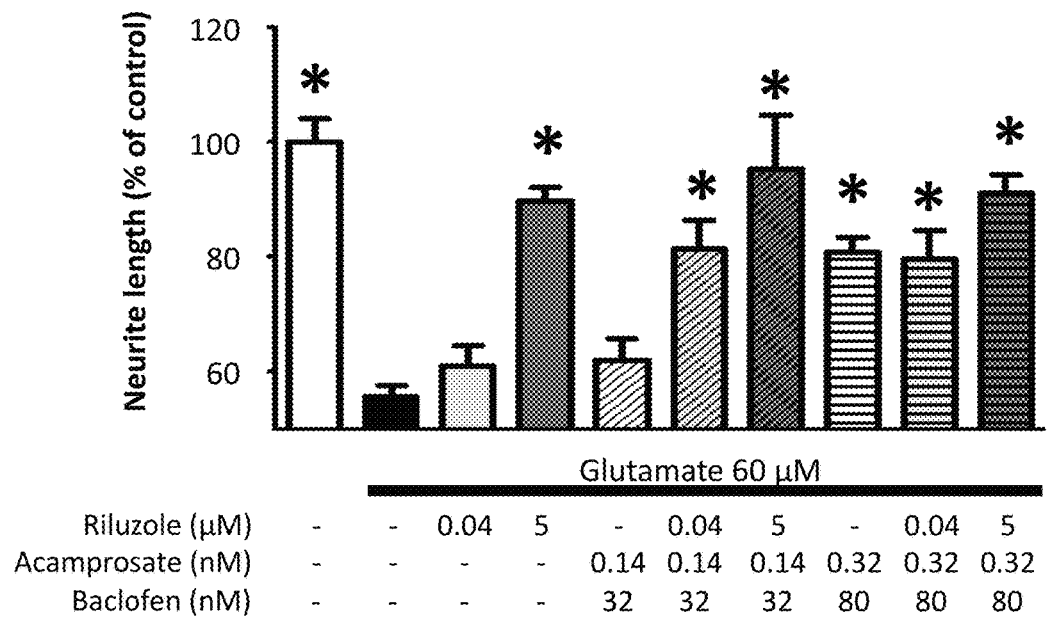

FIGS. 7 A-B: Co-incubation of baclofen-acamprosate combination with riluzole (without riluzole pre-treatment) improves the effect of riluzole alone in protecting neuromuscular junctions against glutamate toxicity in the nerve-muscle cells co-culture model. An important improvement of protection is observed when measuring the number and neurite length of motor units. A) The compositions of the invention significantly improve the beneficial effect of riluzole at 5 μM on motor unit numbers. B) The compositions of the invention significantly improve the effect of riluzole at 0.04 and 5 μM on neurite length. (*: $p<0.05$, significantly different from glutamate toxicity; (Dunnett Post-Hoc test)). White bar: control; black bar: glutamate treatment (60 μM); light grey bar: riluzole treatment (0.04 nM); dark grey bar: riluzole treatment (5 μM); diagonally dashed bars: treatment with combination of acamprosate and baclofen at 0.14 nM and 32 nM, respectively; horizontally dashed bars: treatment with combination of acamprosate and baclofen at 0.32 nM and 80 nM, respectively.

Figure 8A:
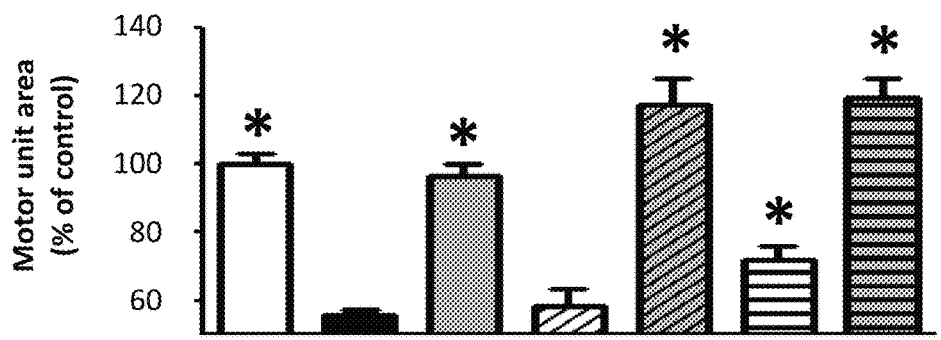
Figure 8B:
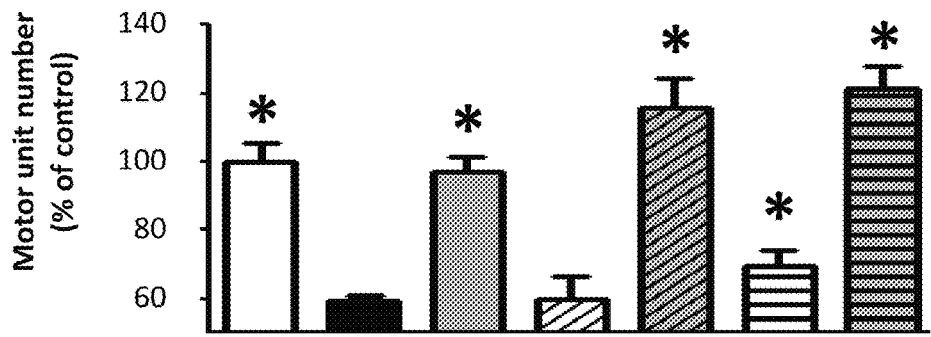
Figure 8C:
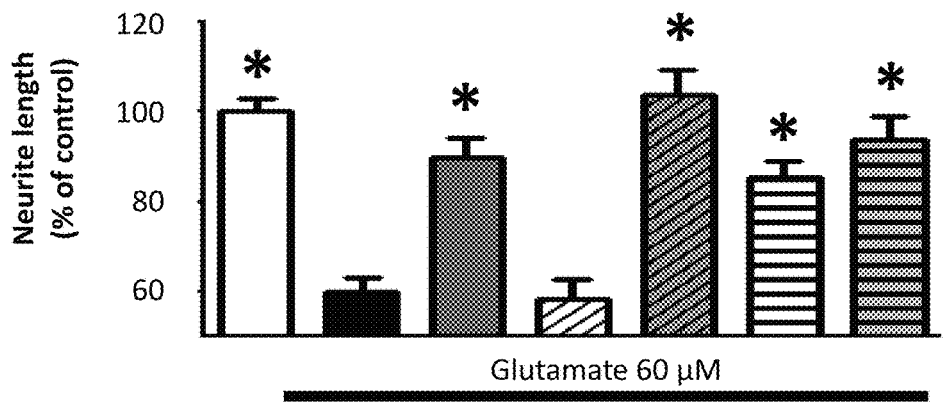

FIGS. 8 A-C: Switching from riluzole treatment to baclofen-acamprosate treatment results in an improved efficiency in the neuromuscular junctions protection as compared to i) riluzole and ii) baclofen-acamprosate therapies. Riluzole (5 µM) is applied for 96 hours, removed and then treatment with the compositions of the invention is applied. A) Riluzole pre-treatment followed by the treatment with baclofen and acamprosate combination improves motor unit area in the glutamate toxicity model. B) Riluzole pre-treatment followed by the treatment with baclofen and acamprosate combination improves motor unit number in the glutamate toxicity model. C) Riluzole pre-treatment followed by the treatment with baclofen and acamprosate combination improves neurite length in the glutamate toxicity model. (*: p<0.05, significantly different from glutamate toxicity; (Dunnett Post-Hoc test)). White bar: control; black bar: glutamate treatment (60 µM); grey bar: riluzole treatment (5 µM); diagonally dashed bars: treatment with combination of acamprosate and baclofen at 0.14 nM and 32 nM, respectively; horizontally dashed bars: treatment with combination of acamprosate and baclofen at 0.32 nM and 80 nM, respectively.

DETAILED DESCRIPTION OF THE INVENTION

The present invention provides new therapeutic approaches for treating ALS or related disorders. More particularly, the present invention discloses novel combinatorial therapies which allow an effective correction of such diseases and may be used in any mammalian subject.

Within the context of this invention, the term "treatment" of a disorder includes the therapy, prophylaxis, retardation or reduction of pain provoked by the disorder. The term treatment includes in particular the control of disease progression and associated symptoms. In relation to ALS, the term treatment also designates a retardation or delayed onset of paralysis, a reduction or prevention of motor neuron degeneration, a reduction of pain, and/or an increase in survival.

The term "ALS related disorders" refers to motor neuron disorders as primary lateral sclerosis (PLS), progressive muscular atrophy (PMA), pseudobulbar palsy and progressive bulbar palsy (PBP), as well as to fronto temporal dementia (FTD).

The term "combination" or "combinatorial treating/therapy" designates a treatment wherein at least two or more drugs are co-administered to a subject to cause a biological effect. In a combined therapy according to this invention, the at least two drugs may be administered together or separately, at the same time or sequentially. Also, the at least two drugs may be administered through different routes and protocols. As a result, although they may be formulated together, the drugs of a combination may also be formulated separately.

As discussed above, the invention relates to drugs compositions and methods for treating ALS or a related disorder in a subject in need thereof.

More particularly, the invention relates to a composition for use in the treatment of ALS or a related disorder, comprising at least two drugs selected from the group consisting of acamprosate, baclofen, cinacalcet, mexiletine, sulfisoxazole and torasemide, or salts or prodrugs or derivatives of any purity or sustained release formulations thereof.

The inventors have surprisingly found that these compounds, in combination(s), show a protective activity against glutamate toxicity, which is one of the causes of neuronal death, in an in vitro model for ALS.

More particularly, the invention shows that drugs of the invention exert a surprising protective activity on motor neurons against glutamate toxicity, which is one of the etiological causes of nerve degeneration in ALS. Moreover, the inventors have observed that these compounds, at low doses, act synergistically to efficiently protect motor units. This is a particularly substantial advantage, which avoids any potential side effects. Moreover, as shown in the experimental part, these combination therapies can delay the onset of paralysis in vivo in animal models of ALS, and prolong life duration. These combination therapies therefore represent substantial improvement in the treatment of ALS subjects.

Accordingly, the invention relates to a composition for use in the treatment of ALS or a related disorder, comprising at least two drugs selected from acamprosate, baclofen, cinacalcet, mexiletine, sulfisoxazole and torasemide, or salt(s) or prodrug(s) or derivative(s) of any purity or sustained release formulations thereof.

The invention also relates to a method for treating ALS or a related disorder in a subject in need thereof, comprising administering to the subject at least two drugs selected from the group consisting of acamprosate, baclofen, cinacalcet, mexiletine, sulfisoxazole and torasemide, or salt(s) or prodrug(s) or derivative(s) of any purity or sustained release formulations thereof.

The invention also relates to a compound selected from acamprosate, baclofen, cinacalcet, mexiletine, sulfisoxazole and torasemide, or salt(s) or prodrug(s) or derivative(s) of any purity or sustained release formulations thereof, in combination with at least one second compound selected from acamprosate, baclofen, cinacalcet, mexiletine, sulfisoxazole and torasemide, or salt(s) or prodrug(s) or derivative(s) of any purity or sustained release formulations thereof, for use in the treatment of ALS or a related disorder by combined, separate or sequential administration to a subject in need thereof.

Preferred combinations for use in the present invention comprise at least one of the following drug combinations, for simultaneous, sequential or separate administration:
 baclofen and cinacalcet,
 cinacalcet and acamprosate,
 baclofen and acamprosate,
 baclofen and acamprosate and torasemide,
 mexiletine and cinacalcet,
 torasemide and baclofen, or
 torasemide and sulfisoxazole,
 or salt(s) or prodrug(s) or derivative(s) of any purity or sustained release formulations thereof for use in the treatment of ALS or a related disorder. Compositions comprising such combinations also represent specific objects of the invention.

The term "prodrug" as used herein refers to any functional derivatives (or precursors) of a compound of the present invention, which, when administered to a biological system (e.g. a human organism), generates said compound as a result of e.g., spontaneous chemical reaction(s), enzyme catalysed chemical reaction(s), and/or metabolic chemical reaction(s). Prodrugs typically have the structure X-drug, wherein X is an inert carrier moiety and drug is the active compound. Prodrugs are usually inactive or less active than the resulting drug and can be used, for example, to improve the physicochemical properties of the drug, to target the drug to a specific tissue, to improve the pharmacokinetic and pharmacodynamic properties of the drug and/or to reduce undesirable side effects. Some of the common functional groups that are amenable to prodrug design include, but are not limited to, carboxylic, hydroxyl, amine, phosphate/phosphonate and carbonyl groups. Prodrugs typically produced via the modification of these groups include, but are not limited to, esters, carbonates, carbamates, amides and phosphates. Specific technical guidance for the selection of suitable prodrugs is general common knowledge [19-23]. Furthermore, the preparation of prodrugs may be performed by conventional methods known by those skilled in the art. Methods which can be used to synthesize other prodrugs are described in numerous reviews on the subject [20,24-30]. For example, arbaclofen placarbil is listed in ChemID plus Advance database (website: chem.sis.nlm.nih.gov/chemidplus/) and arbaclofen placarbil is a well-known prodrug of baclofen [31,32]. Specific examples of prodrugs of baclofen are given in Hanafi et al., 2011 [33], particularly baclofen esters and baclofen ester carbamates, which are of particular interest for CNS targeting. Hence such prodrugs are particularly suitable for compositions of this invention. Arbaclofen placarbil as mentioned before is also a well-known prodrug and may thus be used instead of baclofen in compositions of the invention. Other prodrugs of baclofen can be found in the following patent applications: WO 2010/102071, US 2009/197958, WO 2009/096985, WO 2009/061934, WO 2008/086492, US 2009/216037, WO 2005/066122, US 2011/021571, WO 2003/077902 and WO 2010/120370.

Useful prodrugs for acamprosate such as pantoic acid ester neopentyl sulfonyl esters, neopentyl sulfonyl esters prodrugs or masked carboxylate neopentyl sulfonyl ester prodrugs of acamprosate are notably listed in WO 2009/033069, WO 2009/033061, WO 2009/033054 WO 2009/052191, WO 2009/033079, US 2009/0099253, US 2009/0069419, US 2009/0082464, US 2009/0082440 and US 2009/0076147.

The term "derivative" of a compound includes any molecule that is functionally and/or structurally related to said compound, such as an acid, amide, ester, ether, acetylated variant, hydroxylated variant, or an alkylated (C1-C6) variant of such a compound. The term derivative also includes structurally related compound having lost one or more substituent as listed above. For example, homotaurine is a deacetylated derivative of acamprosate. Preferred derivatives of a compound are molecules having a substantial degree of similarity to said compound, as determined by known methods. Similar compounds along with their index of similarity to a parent molecule can be found in numerous databases such as PubChem (http://pubchem.ncbi.nlm.nih.gov/search/) or DrugBank (http://www.drugbank.ca/). In a more preferred embodiment, derivatives should have a Tanimoto similarity index greater than 0.4, preferably greater than 0.5, more preferably greater than 0.6, even more preferably greater than 0.7 with a parent drug. The Tanimoto similarity index is widely used to measure the degree of structural similarity between two molecules. Tanimoto similarity index can be computed by software such as the Small Molecule Subgraph Detector [34,35] available online (http://www.ebi.ac.uk/thornton-srv/software/SMSD/). Preferred derivatives should be both structurally and functionally related to a parent compound, i.e., they should also retain at least part of the activity of the parent drug, more preferably they should show a protective activity against glutamate toxicity for the motor units (as exemplified in the experimental part).

The term derivatives also include metabolites of a drug, e.g., a molecule which results from the (biochemical) modification(s) or processing of said drug after administration to an organism, usually through specialized enzymatic systems, and which displays or retains a biological activity of the drug. Metabolites have been disclosed as being responsible for much of the therapeutic action of the parent drug. In a specific embodiment, a "metabolite" as used herein designates a modified or processed drug that retains at least part of the activity of the parent drug, more preferably they should show a protective activity against glutamate toxicity for the motor units (as exemplified in the experimental part). Examples of metabolites include hydroxylated forms of torasemide resulting from the hepatic metabolism of the drug (Drug bank database [36]).

The term "salt" refers to a pharmaceutically acceptable and relatively non-toxic, inorganic or organic acid addition salt of a compound of the present invention. Pharmaceutical salt formation consists in pairing an acidic, basic or zwitterionic drug molecule with a counterion to create a salt version of the drug. A wide variety of chemical species can be used in neutralization reaction. Pharmaceutically acceptable salts of the invention thus include those obtained by reacting the main compound, functioning as a base, with an inorganic or organic acid to form a salt, for example, salts of acetic acid, nitric acid, tartric acid, hydrochloric acid, sulfuric acid, phosphoric acid, methane sulfonic acid, camphor sulfonic acid, oxalic acid, maleic acid, succinic acid or citric acid. Pharmaceutically acceptable salts of the invention also include those in which the main compound functions as an acid and is reacted with an appropriate base to form, e.g., sodium, potassium, calcium, magnesium, ammonium, or choline salts. Though most of salts of a given active principle are bioequivalents, some may have, among others, increased solubility or bioavailability properties. Salt selection is now a common standard operation in the process of drug development as taught by H. Stahl and C. G Wermuth in their handbook [37].

In a preferred embodiment, the designation of a compound is meant to designate the compound per se, as well as any pharmaceutically acceptable salt, hydrate, isomer, or racemate thereof.

Table 1 below provides CAS number of compounds for use in the invention, as well as of salt(s), derivative(s), metabolite(s), and/or prodrug(s) of the compounds.

TABLE 1

| Drug | CAS Numbers | Class or Tanimoto similarity index |
|---|---|---|
| acamprosate and related compounds | | |
| acamprosate | 77337-76-9; 77337-73-6 | NA |
| homotaurine | 3687-18-1 | 0.73 |
| ethyl dimethyl ammonio propane sulfonate | / | 0.77 |
| taurine | 107-35-7 | 0.5 |
| baclofen and related compounds | | |
| baclofen | 1134-47-0; 66514-99-6; 69308-37-8; 70206-22-3; 63701-56-4; 63701-55-3 | NA |
| 3-(p-chlorophenyl)-4-hydroxybutyric acid | / | Metabolite |
| arbaclofen placarbil | 847353-30-4 | Prodrug |

TABLE 1-continued

| Drug | CAS Numbers | Class or Tanimoto similarity index |
|---|---|---|
| mexiletine and related compounds | | |
| mexiletine | 31828-71-4; 5370-01-4 | |
| 6-hydroxymethylmexiletine | 53566-98-6 | Metabolite |
| 4-hydroxymexiletine | 53566-99-7 | Metabolite |
| 3-hydroxymexiletine (MHM) | 129417-37-4 | Metabolite |
| N-hydroxymexiletine glucuronide | 151636-18-9 | Metabolite |
| sulfisoxazole and related compounds | | |
| sulfisoxazole | 127-69-5; 4299-60-9 | |
| N(4)-acetylsulfisoxazole | 4206-74-0 | Metabolite |
| sulfisoxazole acetyl | 80-74-0 | Prodrug |
| sulfamethoxazole | 723-46-6 | 0.52 |
| cinacalcet and related compounds | | |
| cinacalcet | 226256-56-0; 364782-34-3 | |
| hydrocinnamic acid | 501-52-0 | Metabolite |
| torasemide and related compounds | | |
| torasemide | 56211-40-6; 72810-59-4 | |
| hydroxytorasemide | 99300-68-2; 99300-67-1 | Metabolites |
| carboxytorasemide | | Metabolite |
| tolbutamide | 64-77-7 | 0.55 |

More preferably, drug compositions of the invention comprise 2, 3, 4 or 5 distinct drugs, even more preferably 2, 3 or 4 distinct drugs for combinatorial treatment of ALS or a related disorder in a subject in need thereof.

In a particular embodiment, the invention relates composition per se comprising baclofen and cinacalcet, or acamprosate and cinacalcet or salt(s) or prodrug(s) or derivative(s) of any purity or sustained release formulations.

In a more particular embodiment, the invention relates to a composition comprising acamprosate and cinaclacet or salt(s) or prodrug(s) or derivative(s) of any purity or sustained release formulations for its use in the treatment of ALS or a related disorder, wherein the daily dosage of acamprosate is equal or lower to 10 mg.

Furthermore, in another particular embodiment, the compositions and methods of the invention further use riluzole, or a salt, prodrug, derivative of any purity, or sustained release formulation thereof. The results presented indeed surprisingly show that, when used in combination with riluzole (CAS n° 1744-22-5), compositions of the invention can substantially increase the clinical benefit of the treatment to patients.

Accordingly, a particular object of this invention is a composition comprising i) at least one drug selected from acamprosate, baclofen, cinacalcet, mexiletine, sulfisoxazole and torasemide, and ii) riluzole, for a simultaneous, separate or sequential use in the treatment of ALS or a related disorder.

Another particular object of this invention is a composition as disclosed above, comprising i) at least two drugs selected from acamprosate, baclofen, cinacalcet, mexiletine, sulfisoxazole and torasemide, and ii) riluzole, for a simultaneous, separate or sequential use in the treatment of ALS or a related disorder.

A preferred object of this invention is a composition comprising at least one of the following drug combinations:
riluzole, baclofen and cinacalcet,
riluzole, cinacalcet and acamprosate,
riluzole, baclofen and acamprosate,
riluzole, baclofen and acamprosate and torasemide,
riluzole, mexiletine and cinacalcet,
riluzole, torasemide and baclofen, or
riluzole, torasemide and sulfisoxazole,
or salt(s) or prodrug(s) or derivative(s) of any purity or sustained release formulations thereof, for a simultaneous, separate or sequential use in the treatment of ALS or a related disorder.

Other additional therapies that can be used in conjunction with drug combination(s) according to the present invention, may comprise one or more drug(s) that ameliorate(s) symptoms of ALS, one or more drug(s) that could be used for palliative treatment of ALS or one or more drug(s) currently evaluated in the frame of clinical trials for treating of ALS. Preferably, said one or more drug(s) is/are selected from AEOL 10150, arimoclomol, AVP-923, botulinum toxin type B (Myobloc), ceftriaxone, celastrol, celecoxib, cistanche total glycosides, coenzyme Q10, copaxone, creatine, creatinine, dronabinol, erythropoietin, escitalopram (Lexapro), glatiramer acetate, granulocyte-colony stimulating factor (G-CSF), growth hormone (Somatropin), GSK1223249, indinavir, insulin-like growth factor-1 (IGF-I), IGF-1-AAV, KNS-760704, leteprinim, leuprolide, levetiracetam, MCI-186, mecobalamin, minocycline, modafinil, Naaladase inhibitor, N-Acetylcysteine, NBQX, nimesulide, nimodipine, olanzapine, olesoxime (TRO19622), ONO-2506, oxepa, pioglitazone, R(+) pramipexole dihydrochloride monohydrate, olesoxime, oxandrolone, quinidine, phenyl butyrate, SB-509, Scriptaid, sNN0029, somatropine, talampanel, tamoxifen, tauroursodeoxycholic acid, TCH346, testosterone, thalidomide, trehalose, tretinoin, vitamin E, YAM80 or from 17-beta-estradiol, 2-MPPA (2-(3-mercaptopropyl)pentanedioic acid), 3,4-diaminopyridine, 5-hydroxytryptophan, 7-nitroindazole, alpha-lipoic acid, AM1241, aminophylline, angiogenin, anti-human SOD1 antibody, antisense peptide nucleic acid directed against p75(NTR), AP7, apocynin, BAPTA-AM, BDNF, BN82451, cannabinol, cardiotrophin-1, CD4 antibodies, CNTF, colivelin, dietary copper, corticotrophin, cyclophosphamide, Delta (9)-tetrahydrocannabinol, DHEA, diazepam, dietary zinc, diltiazem, DMPO, DP-109, DP-460, edaravone, EGCG, epigallocatechin gallate, etidronate, FeTCPP, fluvoxamine, folic acid, gabapentin, galectin-1, GDNF, ginseng, GPI-1046, guanidine, HGF, humanin, IFN-alpha, interleukin-3, ivermectin, L-745,870, L-carnitine, L-DOPA, lecithinized SOD, lenalidomide, leupeptin, LIF, L-NAME, lysine acetylsalicylate, melatonin, mepivacaine, methamphetamine, methylcobalamin, MK-801, MnTBAP, modafinil, morphine, Neu2000, NGF, nordihydroguaiaretic acid, nortriptyline, NT3, olmesartan, penicillamine, pentoxifylline, pimozide, polyamine-modified catalase, pramipexole, prednisone, progesterone, promethazine, putrescine-modified catalase, pyruvate, rasagiline, RK35, Ro 28-2653, rofecoxib, RPR 119990, RX77368, SB203580, selegiline, semapimod, sertraline, SS-31, SSR180575, stabilized siRNA against human Cu,Zn-superoxide dismutase (SOD1), tacrolimus, tamsulosin hydrochloride, TAT-modified Bcl-X(L), TGF-beta2, tianeptine, trientine, TRO19622, U-74389F, VEGF, vincristine, WHI-P131, WIN55, 212-2, WX-340, xaliproden, ZK 187638 and zVAD-fmk.

As indicated above, the preferred therapies of this invention contains 2, 3, 4 or even more distinct active compounds, which may optionally be further associated or combined with other treatment(s). In a combination therapy of this invention, the compounds or drugs may be formulated together or separately, and administered together, separately or sequentially.

The invention also relates to a method of treating ALS disease or a related disorder, the method comprising simultaneously, separately or sequentially administering to a subject in need thereof a drug combination as disclosed above.

The drugs or compositions of the invention may be administered repeatedly to the subject.

The compositions of the invention typically comprise one or several pharmaceutically acceptable carriers or excipients.

A further object of this invention relates to the use of at least two drugs selected from the group consisting of acamprosate, baclofen, cinacalcet, mexiletine, sulfisoxazole and torasemide for the manufacture of a medicament for the treatment of ALS or a related disorder by combined, separate or sequential administration to a subject in need thereof.

A further object of this invention relates to the use of at least one of the following drug combinations:
baclofen and cinacalcet,
cinacalcet and acamprosate,
baclofen and acamprosate,
baclofen and acamprosate and torasemide,
mexiletine and cinacalcet,
torasemide and baclofen, or
torasemide and sulfisoxazole,
for the manufacture of a medicament for the treatment of ALS or a related disorder by combined, separate or sequential administration to a subject in need thereof.

In a particular embodiment, the invention also relates to the use of at least one drug selected from the group consisting of acamprosate, baclofen, cinacalcet, mexiletine, sulfisoxazole and torasemide in a combination with the riluzole for the manufacture of a medicament for the treatment of ALS or a related disorder by combined, separate or sequential administration to a subject in need thereof.

Another embodiment relates to the use of at least two drugs selected from the group consisting of acamprosate, baclofen, cinacalcet, mexiletine, sulfisoxazole and torasemide in a combination with the riluzole for the manufacture of a medicament for the treatment of ALS or a related disorder by combined, separate or sequential administration to a subject in need thereof.

In a more particular embodiment, of this invention relates to the use of at least one of the following drug combinations:
baclofen and cinacalcet,
cinacalcet and acamprosate,
baclofen and acamprosate,
baclofen and acamprosate and torasemide,
mexiletine and cinacalcet,
torasemide and baclofen, or
torasemide and sulfisoxazole,
in a combination with riluzole, for the manufacture of a medicament for the treatment of ALS or a related disorder by combined, separate or sequential administration to a subject in need thereof.

A further object of this invention is a method of preparing a pharmaceutical composition, the method comprising mixing the above compounds in an appropriate excipient or carrier.

Therapy according to the invention may be provided at home, the doctor's office, a clinic, a hospital's outpatient department, or a hospital, so that the doctor can observe the therapy's effects closely and make any adjustments that are needed.

The duration of the therapy depends on the stage of the disease, the age and condition of the patient, and how the patient responds to the treatment.

Additionally, a person having a greater risk of developing an additional neuropathic disorder (e.g., a person who is genetically predisposed to or have, for example, diabetes, or is being under treatment for an oncological condition, etc.) may receive prophylactic treatment to alleviate or to delay eventual neuropathic response.

The dosage, frequency and mode of administration of each drug can be controlled independently. Combination therapy may be given in on-and-off cycles that include rest periods so that the patient's body has a chance to recovery from any as yet unforeseen side-effects. The drugs may also be formulated together such that one administration delivers both drugs.

Formulation of Pharmaceutical Compositions

The administration of each drug of the combination may be by any suitable means that results in a concentration of the drug that, combined with the other component, is able to ameliorate the patient condition.

While it is possible for the active ingredients of the combination to be administered as the pure chemical it is preferable to present them as a pharmaceutical composition, also referred to in this context as pharmaceutical formulation. Possible compositions include those suitable for oral, rectal, topical (including transdermal, buccal and sublingual), or parenteral (including subcutaneous, intramuscular, intravenous and intradermal) administration.

More commonly these pharmaceutical formulations are prescribed to the patient in "patient packs" containing a number dosing units or other means for administration of metered unit doses for use during a distinct treatment period in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in traditional prescriptions. The inclusion of a package insert has been shown to improve patient compliance with the physician's instructions. Thus, the invention further includes a pharmaceutical formulation, as herein before described, in combination with packaging material suitable for said formulations. In such a patient pack the intended use of a formulation for the combination treatment can be inferred by instructions, facilities, provisions, adaptations and/or other means to help using the formulation most suitably for the treatment. Such measures make a patient pack specifically suitable for and adapted for use for treatment with the combination of the present invention.

The drug may be contained in any appropriate amount in any suitable carrier substance, and is may be present in an amount of 1-99% by weight of the total weight of the composition. The composition may be provided in a dosage form that is suitable for the oral, parenteral (e.g., intravenously, intramuscularly), rectal, cutaneous, nasal, vaginal, inhalant, skin (patch), or ocular administration route. Thus, the composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, or aerosols.

The pharmaceutical compositions may be formulated according to conventional pharmaceutical practice (see, e.g., Gennaro [38] and the Encyclopedia of Pharmaceutical Technology [39]).

Pharmaceutical compositions according to the invention may be formulated to release the active drug substantially immediately upon administration or at any predetermined time or time period after administration.

The controlled release formulations include (i) formulations that create a substantially constant concentration of the drug within the body over an extended period of time; (ii) formulations that after a predetermined lag time create a substantially constant concentration of the drug within the body over an extended period of time; (iii) formulations that sustain drug action during a predetermined time period by maintaining a relatively, constant, effective drug level in the body with concomitant minimization of undesirable side effects associated with fluctuations in the plasma level of the active drug substance; (iv) formulations that localize drug action by, e.g., spatial placement of a controlled release composition adjacent to or in the diseased tissue or organ; and (v) formulations that target drug action by using carriers or chemical derivatives to deliver the drug to a particular target cell type.

Administration of drugs in the form of a controlled release formulation is especially preferred in cases in which the drug in combination, has (i) a narrow therapeutic index (i.e., the difference between the plasma concentration leading to harmful side effects or toxic reactions and the plasma concentration leading to a therapeutic effect is small; in general, the therapeutic index, TI, is defined as the ratio of median lethal dose (LD50) to median effective dose (ED50)); (ii) a narrow absorption window in the gastro-intestinal tract; or (iii) a very short biological half-life so that frequent dosing during a day is required in order to sustain the plasma level at a therapeutic level.

Any of a number of strategies can be pursued in order to obtain controlled release in which the rate of release outweighs the rate of metabolism of the drug in question. Controlled release may be obtained by appropriate selection of various formulation parameters and ingredients, including, e.g., various types of controlled release compositions and coatings. Thus, the drug is formulated with appropriate excipients into a pharmaceutical composition that, upon administration, releases the drug in a controlled manner (single or multiple unit tablet or capsule compositions, oil solutions, suspensions, emulsions, microcapsules, microspheres, nanoparticles, patches, and liposomes).

Solid Dosage Forms for Oral Use

Preferred administration route for cilostazol and for riluzole is the oral route. Formulations for oral use include tablets containing the active ingredient(s) in a mixture with non-toxic pharmaceutically acceptable excipients. These excipients may be, for example, inert excipients or fillers (e.g., sucrose, microcrystalline cellulose, starches including potato starch, calcium carbonate, sodium chloride, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., acacia, alginic acid, sodium alginate, gelatin, starch, pregelatinized starch, microcrystalline cellulose, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., stearic acid, silicas, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active drug substance in a predetermined pattern (e.g., in order to achieve a controlled release formulation) or it may be adapted not to release the active drug substance until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). A time delay material such as, e.g., glyceryl monostearate or glyceryl distearate may be employed.

The solid tablet compositions may include a coating adapted to protect the composition from unwanted chemical changes, (e.g., chemical degradation prior to the release of the active drug substance). The coating may be applied on the solid dosage form in a similar manner as that described in Encyclopedia of Pharmaceutical Technology [39].

The drugs may be mixed together in the tablet, or may be partitioned. For example, a first drug is contained on the inside of the tablet, and a second drug is on the outside, such that a substantial portion of the second drug is released prior to the release of the first drug.

Formulations for oral use may also be presented as chewable tablets, or as hard gelatin capsules wherein the active ingredient is mixed with an inert solid excipient (e.g., potato starch, microcrystalline cellulose, calcium carbonate, calcium phosphate or kaolin), or as soft gelatin capsules wherein the active ingredient is mixed with water or an oil medium, for example, liquid paraffin, or olive oil. Powders and granulates may be prepared using the ingredients mentioned above under tablets and capsules in a conventional manner.

Controlled release compositions for oral use may, e.g., be constructed to release the active drug by controlling the dissolution and/or the diffusion of the active drug substance.

Dissolution or diffusion controlled release can be achieved by appropriate coating of a tablet, capsule, pellet, or granulate formulation of drugs, or by incorporating the drug into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

A controlled release composition containing one or more of the drugs of the claimed combinations may also be in the form of a buoyant tablet or capsule (i.e., a tablet or capsule that, upon oral administration, floats on top of the gastric content for a certain period of time). A buoyant tablet formulation of the drug(s) can be prepared by granulating a mixture of the drug(s) with excipients and 20-75% w/w of hydrocolloids, such as hydroxyethylcellulose, hydroxypropylcellulose, or hydroxypropyl-methylcellulose. The obtained granules can then be compressed into tablets. On contact with the gastric juice, the tablet forms a substantially water-impermeable gel barrier around its surface. This gel barrier takes part in maintaining a density of less than one, thereby allowing the tablet to remain buoyant in the gastric juice.

Liquids for Oral Administration

Powders, dispersible powders, or granules suitable for preparation of an aqueous suspension by addition of water are convenient dosage forms for oral administration. Formulation as a suspension provides the active ingredient in a mixture with a dispersing or wetting agent, suspending agent, and one or more preservatives. Suitable suspending agents are, for example, sodium carboxymethylcellulose, methylcellulose, sodium alginate, and the like.

Parenteral Compositions

Although less preferred, the pharmaceutical composition may also be administered parenterally by injection, infusion or implantation (intravenous, intramuscular, subcutaneous, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation.

Compositions for parenteral use may be provided in unit dosage forms (e.g., in single-dose ampoules), or in vials containing several doses and in which a suitable preservative may be added (see below). The composition may be in form of a solution, a suspension, an emulsion, an infusion device, or a delivery device for implantation or it may be presented as a dry powder to be reconstituted with water or another suitable vehicle before use. Apart from the active drug(s), the composition may include suitable parenterally acceptable carriers and/or excipients. The active drug(s) may be incorporated into microspheres, microcapsules, nanoparticles, liposomes, or the like for controlled release. The composition may include suspending, solubilizing, stabilizing, pH-adjusting agents, and/or dispersing agents.

The pharmaceutical compositions according to the invention may be in the form suitable for sterile injection. To prepare such a composition, the suitable active drug(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution. The aqueous formulation may also contain one or more preservatives (e.g., methyl, ethyl or n-propyl p-hydroxybenzoate). In cases where one of the drugs is only sparingly or slightly soluble in water, a dissolution enhancing or solubilizing agent can be added, or the solvent may include 10-60% w/w of propylene glycol or the like.

Controlled release parenteral compositions may be in form of aqueous suspensions, microspheres, microcapsules, magnetic microspheres, oil solutions, oil suspensions, or emulsions. Alternatively, the active drug(s) may be incorporated in biocompatible carriers, liposomes, nanoparticles, implants, or infusion devices. Materials for use in the preparation of microspheres and/or microcapsules are, e.g., biodegradable/bioerodible polymers such as polygalactin, poly-(isobutyl cyanoacrylate), poly(2-hydroxyethyl-L-glutamine). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(glycolic acid) or poly(ortho esters)).

Alternative Routes

Although less preferred and less convenient, other administration routes, and therefore other formulation, may be contemplated. In this regard, for rectal application, suitable dosage forms for a composition include suppositories (emulsion or suspension type), and rectal gelatin capsules (solutions or suspensions). In a typical suppository formulation, the active drug(s) are combined with an appropriate pharmaceutically acceptable suppository base such as cocoa butter, esterified fatty acids, glycerinated gelatin, and various water-soluble or dispersible bases like polyethylene glycols. Various additives, enhancers, or surfactants may be incorporated.

The pharmaceutical compositions may also be administered topically on the skin for percutaneous absorption in dosage forms or formulations containing conventionally non-toxic pharmaceutical acceptable carriers and excipients including microspheres and liposomes. The formulations include creams, ointments, lotions, liniments, gels, hydrogels, solutions, suspensions, sticks, sprays, pastes, plasters, and other kinds of transdermal drug delivery systems. The pharmaceutically acceptable carriers or excipients may include emulsifying agents, antioxidants, buffering agents, preservatives, humectants, penetration enhancers, chelating agents, gel-forming agents, ointment bases, perfumes, and skin protective agents.

The emulsifying agents may be naturally occurring gums (e.g., gum acacia or gum tragacanth).

The preservatives, humectants, penetration enhancers may be parabens, such as methyl or propyl p-hydroxybenzoate, and benzalkonium chloride, glycerin, propylene glycol, urea, etc.

The pharmaceutical compositions described above for topical administration on the skin may also be used in connection with topical administration onto or close to the part of the body that is to be treated. The compositions may be adapted for direct application or for application by means of special drug delivery devices such as dressings or alternatively plasters, pads, sponges, strips, or other forms of suitable flexible material.

Dosages and Duration of the Treatment

It will be appreciated that the drugs of the combination may be administered concomitantly, either in the same or different pharmaceutical formulation or sequentially. If there is sequential administration, the delay in administering one of the active ingredients should not be such as to lose the benefit of the efficacious effect of the combination of the active ingredients. A minimum requirement for a combination according to this description is that the combination should be intended for combined use with the benefit of the efficacious effect of the combination of the active ingredients. The intended use of a combination can be inferred by facilities, provisions, adaptations and/or other means to help using the combination according to the invention.

One remarkable advantage of the invention is that each compound may be used at low doses in a combination therapy, while producing, in combination, a substantial clinical benefit to the patient. The combination therapy may indeed be effective at doses where the compounds have individually low or no effect. Accordingly, a particular advantage of the invention lies in the ability to use sub-optimal doses of each compound, i.e., doses which are lower than therapeutic doses usually prescribed, preferably ½ of therapeutic doses, more preferably ⅓, ¼, ⅕, or even more preferably ¹/₁₀ of therapeutic doses. In particular examples, doses as low as ¹/₂₀, ¹/₃₀, ¹/₅₀, ¹/₁₀₀, or even lower, of therapeutic doses are used.

In a particular embodiment such conjunction of molecular effects can further lead to synergistic combinations. Synergy may be assessed by methods known well known by those skilled in the art. For instance, synergy can be characterized by using a two way ANOVA to determine whether the interaction between each drugs is significant or not (i.e. synergy, [40]), or by calculating a combinatory index from the dose effect curves of each of the compounds alone and of their combinations [41,42].

At such sub-therapeutic dosages, the compounds would exhibit no side effect, while the combination(s) according to the invention are fully effective in treating ALS or a related disorder.

A preferred dosage corresponds to amounts from 1% up to 50% of those usually prescribed for long-term maintenance treatment.

The most preferred dosage may correspond to amounts from 1% up to 10% of those usually prescribed for long-term maintenance treatment.

A therapeutically effective amount of cilostazol is an amount suitable for preventing or reducing the risk of developing ALS disease and halting or slowing the progression of ALS disease once it has become clinically manifest.

Preferred examples of dosages according to the invention are:
mexiletine: from about 6 to 120 mg per day, preferably less than 60 mg per day, more preferably less than 30 mg per day, even more preferably less than 15 mg per day, such dosages being particularly suitable for oral administration,
torasemide: from about 0.05 to 4 mg per day, preferably less than 2 mg per day, more preferably less than 1 mg per day, even more preferably less than 0.5 mg per day, such dosages being particularly suitable for oral administration,
acamprosate: between 1 to 1000 mg per day, preferably less than 500 mg per day, preferably less than 400 mg per day, more preferably less than 200 mg per day, even more preferably less than 50 mg per day, or even less than 10 mg per day, even more preferably from about 0.1 to 100 mg per day, furthermore preferably between 0.5 mg and 100 mg, typically 0.8 mg per day, 2 mg per day, 20 mg per day, 40 mg per day, or 80 mg per day, such dosages being particularly suitable for oral administration,
baclofen: between 0.01 to 150 mg per day, preferably less than 100 mg per day, more preferably less than 50 mg per day, even more preferably less than 30 mg per day, typically 12 mg per day, 24 mg per day, 30 mg per day, such dosages being particularly suitable for oral administration,
cinacalcet: from about 0.3 to 150 mg per day, preferably less than 100 mg per day, preferably less than 50 mg per day, more preferably less than 36 mg per day, and even more preferably between 0.3 and 25 mg per day, such dosages being particularly suitable for oral administration,
sulfisoxazole: 800 mg per day or less, preferably less than 400 mg, more preferably less than 200 mg per day, more preferably less than 100 mg per day, even more preferably less than 20 mg per day, such dosages being particularly suitable for oral administration,
riluzole: from about 0.01 to 100 mg per day, preferably less than 75 mg per day, more preferably less than 50 mg per day, even more preferably less than 25 mg per day, such dosages being particularly suitable for oral administration.

A more particular object of the invention is a tablet suitable for the administration of any of therapy of the invention, comprising baclofen, acamprosate and riluzole. In an even more particular embodiment, said tablet is cleavable in 2, 3 and/or 4 part as a function of the dose to be administered at each taking.

Alternatively, where a separate administration would be considered more proper, combinations of the invention can be provided under the form of a unit dosage package, such unit dosage package being configured to hold a first unit dosage comprising acamprosate and baclofen and a second unit dosage comprising riluzole. In a particular embodiment unit dosages are tablets.

It will be understood that the amount of the drug actually administered will be determined by a physician, in the light of the relevant circumstances including the condition or conditions to be treated, the exact composition to be administered, the age, weight, and response of the individual patient, the severity of the patient's symptoms, and the chosen route of administration. Additionally, pharmacogenomic (the effect of genotype on the pharmacokinetic, pharmacodynamic or efficacy profile of a therapeutic) information about a particular patient may affect the dosage used. Therefore, the above dosage ranges are intended to provide general guidance and support for the teachings herein, but are not intended to limit the scope of the invention.

Although the active drugs of the present invention may be administered in divided doses, for example two or three times daily, a single daily dose of each drug in the combination is preferred, with a single daily dose of all drugs in a single pharmaceutical composition (unit dosage form) being most preferred. The term "unit dosage form" refers to physically discrete units (such as capsules, tablets, or loaded syringe cylinders) suitable as unitary dosages for human subjects, each unit containing a predetermined quantity of active material or materials calculated to produce the desired therapeutic effect, in association with the required pharmaceutical carrier.

Administration can be one to several times daily for several days to several years, and may even be for the life of the patient. Chronic or at least periodically repeated long-term administration will be indicated in most cases.

In a most preferred embodiment, combinations of the invention are used in a combination with riluzole, wherein all the drugs are administered orally. In such protocol, riluzole is preferably administered repeatedly, e.g., daily, more preferably at a daily dosage of 0.01-100 mg per day, even more preferably at a daily dosage of 0.1-100 mg per day, most preferably between 0.1-50 mg per day, and the other drugs at the above indicated dosages.

The drugs may be administered simultaneously, i.e., approximately at the same time, although not necessarily exactly at the same time or through the same formulation. In particular, riluzole may be formulated separately from the other drugs and all being ingested at approximately the same period of the day, to ensure they are present and can act in combination in the body. It is also possible to define a therapeutic protocol where riluzole is administered in alternation with the combination comprising of at least two drugs selected from acamprosate, baclofen, cinacalcet, mexiletine, sulfisoxazole and torasemide (e.g., one day riluzole, the following day the said combination, and so on). It should be noted that various protocols may be adjusted or defined by the physician, ensuring the combination therapy of the invention is most effective in each patient.

The following examples are given for purposes of illustration and not by way of limitation.

EXAMPLES

Protective Effect of Drug Combinations in Models of ALS

Combination therapies according to the present invention are tested in vitro, on rat cortical cells, in a nerve-muscle co-culture model, and in vivo, in a mouse model of ALS. Protocols and results are presented in this section.

All animal experiments were carried out according to the National Institute of Health (NIH) guidelines for the care and use of laboratory animals, and approved by the National Animal Experiment Board.

1. Protective Effect Against Glutamate Toxicity in Primary Cultures of Neuronal Cells.

Glutamate toxicity is involved in the pathogenesis of ALS. In this set of experiment, candidate compounds have been tested for their ability to prevent or reduce the toxic effects of glutamate on neuronal cells. The drugs are first tested individually, followed by assays of their combinatorial action.

Neuronal Cell Preparation

The efficacy of drug combinations of the invention was first assessed on primary cortical neuron cells.

Rat cortical neurons were cultured as described by Singer et al. [43]. Briefly pregnant female rats of 15 days gestation were killed by cervical dislocation (Rats Wistar) and the foetuses were removed from the uterus. The cortex was removed and placed in ice-cold medium of Leibovitz (L15) containing 2% of penicillin 10.000 U/mL and streptomycin 10 mg/mL and 1% of bovine serum albumin (BSA). Cortices were dissociated by trypsin for 20 min at 37° C. (0.05%). The reaction was stopped by the addition of Dulbecco's modified Eagle's medium (DMEM) containing DNase1 grade II and 10% of foetal calf serum (FCS). Cells were then mechanically dissociated by 3 serial passages through a 10 mL pipette and centrifuged at 515 g for 10 min at +4° C. The supernatant was discarded and the pellet of cells was re-suspended in a defined culture medium consisting of Neurobasal supplemented with B27 (2%), L-glutamine (0.2 mM), 2% of PS solution and 10 ng/mL of brain-derived neurotrophic factor (BDNF). Viable cells were counted in a Neubauer cytometer using the trypan blue exclusion test. The cells were seeded at a density of 30 000 cells/well in 96 well-plates (wells were pre-coated with poly-L-lysine (10 µg/mL)) and were cultured at +37° C. in a humidified air (95%)/CO2 (5%) atmosphere.

Glutamate Toxicity Assays

The neuroprotective effect of compounds was assessed by quantification of the neurite network (neurofilament immunostaining) which specifically reveals the glutamatergic neurons.

After 12 days of neuron culture, drugs of the candidate combinations were solved in culture medium (+0.1% DMSO). Candidate combinations were then pre-incubated with neurons for 1 hour before the Glutamate injury. One hour after incubation with candidate combinations, glutamate was added for 20 min, to a final concentration of 40 µM, in presence of candidate combinations, in order to avoid further drug dilutions. At the end of the incubation, medium was changed with medium with candidate combination but without glutamate. The culture was fixed 24 hours after glutamate injury. MK801 (dizocilpinehydrogen maleate, 77086-22-7—20 µM) was used as a positive control.

After permeabilization with saponin (Sigma), cells were blocked for 2 hours with PBS containing 10% goat serum, then the cells were incubated with mouse monoclonal primary antibody against Neurofilament antibody (NF, Sigma). This antibody was revealed with Alexa Fluor 488 goat anti-mouse IgG.

Nuclei of cells were labeled by a fluorescent marker (Hoechst solution, Sigma), and neurite network quantified. Six wells per condition were used to assess neuronal survival in 3 different cultures.

Results

All of the tested drug combinations give a protective effect against glutamate toxicity for cortical neuronal cells. Results are shown in Table 2 below.

As exemplified in FIGS. 1, 3 and 4, combinations of the invention strongly protect neurons from glutamate toxicity under the experimental conditions described above. It is noteworthy that an effective protection is noticed using drug concentrations at which drugs used alone have no significant or lower protective effect.

Indeed, as exemplified in FIG. 3, mexiletine-cinacalcet combination efficiently protects neuronal cells from glutamate toxicity, whereas no protection is afforded by the single drugs. Baclofen-acamprosate (FIG. 1) combination gives a protective effect against glutamate toxicity for cortical neuronal cells. Combination of baclofen and acamprosate induces an improvement of more than 200% compared to acamprosate alone and more than 47% compared to baclofen used alone. Sulfisoxazole-torasemide combination (FIG. 4) induces an improvement of about 400% than that provided by torasemide alone at the same concentration, and of more than 800% than that observed when sulfisoxazole is used alone at the same concentration.

TABLE 2

| Drug Combination | Neuroprotective effect against glutamate toxicity |
|---|---|
| baclofen and torasemide | + |
| baclofen-acamprosate-torasemide | + |
| mexiletine and cinacalcet | + |
| sulfisoxazole and torasemide | + |
| baclofen and acamprosate | + |
| acamprosate and cinacalcet | + |
| baclofen and cinacalcet | + |

2. Protective Effect Against Glutamate Toxicity in Primary Cultures of Nerve-Muscle Co-Culture.

Primary Cocultures of Nerve- and Muscle Cells

Human muscle is prepared according to a previously described method from portions of biopsy of a healthy subject [44]. Muscle cells are established from dissociated cells (20 000 cells per wells), plated in gelatin-coated 0.1% on 48 wells plate and grown in a proliferating medium consisting of mix of 75% of MEM medium with 25% of M199 medium supplemented with glutamine 2 mM, bovine insulin 10 µg/mL, human recombinant epidermal growth factor 10 ng/mL, human recombinant fibroblast growth factor basic 2 ng/mL, FCS 10% and 2% penicillin 10 000 U/mL and streptomycin (10 mg/mL).

Immediately after satellite cells fusion, whole transverse slices of 13-day-old rat Wistar embryos spinal cords with 4 dorsal root ganglia (DRG) attached are placed on the muscle monolayer (one explant per well, in center area). DRG are necessary to achieve a good ratio of innervations. Innervated cultures are maintained in a mixed medium (75% of MEM with 25% of M199), supplemented with glutamine 2 mM, 5% FCS, bovine insulin 5 µg/mL, and 2% penicillin 10 000 U/mL and streptomycin (10 mg/mL).

After 24 hours of co-culture, neurites are observed growing out of the spinal cord explants. They make contacts with myotubes and induce the first contractions after about 8 days. Quickly thereafter, innervated muscle fibres located in proximity to the spinal cord explants, are virtually continuously contracting. Innervated fibres are morphologically and spatially distinct from the non-innervated ones and could easily be distinguished from them.

Glutamate Injury

On day 27, co-cultures are incubated with candidate compounds, combination thereof or riluzole one hour before glutamate intoxication (60 µM) for 20 min. Then, co-cultures are washed and candidate compounds, combination thereof, and/or riluzole are added for an additional 48 hours. After this incubation time, unfixed co-cultures are incubated with α-bungarotoxin coupled with Alexa 488 at concentration 500 nmol/L for 15 min at room temperature. Then, co-cultures fixed by paraformaldehyde for 20 min at room temperature. After permeabilization with 0.1% of saponin, co-cultures are incubated with NF (dilution 1/400).

These antibodies are detected with Alexa Fluor 568 goat anti-mouse IgG (Molecular probe, 1/400 dilution), nuclei of neurons are labeled by a fluorescent marker (Hoechst solution, 1 µg/mL in the same solution).

Endpoints are (1) total neurite length, (2) number of motor units, (3) total motor unit area, which are indicative of motor neuron survival and functionality.

For each condition, 2×10 pictures per well are taken using InCell Analyzer™ 1000 (GE Healthcare) with 20× magnification. All the images are taken in the same conditions.

Glutamate Injury with Riluzole Pre-Treatment

On day 23 (i.e. 4 days of pre-treatment), co-cultures are incubated with riluzole. After 4 days (i.e. on day 27), drug combinations are added one hour before glutamate addition and then glutamate (60 µM) is added for 20 min. Cocultures are then treated for immunofluorescence analysis as stated above.

In another set of experiments, the same protocol than above is performed except that riluzole is removed from cultures when said drug combinations are added (i.e. after the 4 days riluzole pre-treatment) ("switch" experiments).

Results

A significant protection is noticed for all the three endpoints when drugs are used in combination, at concentrations where, when used alone, no effect is noticed. Tested drug combinations are listed in Table 3 and exemplified in FIG. 2. This unexpected synergistic effect allows using drugs at doses so low that potential side effects should be overcome.

TABLE 3

| Drug Combination | Protective effect against glutamate intoxication in muscle/nerve co-cultures |
|---|---|
| baclofen and cinacalcet | + |
| cinacalcet and acamprosate | + |
| baclofen-torasemide | + |
| baclofen-acamprosate-torasemide | + |
| mexiletine and cinacalcet | + |
| sulfisoxazole and torasemide | + |
| baclofen and acamprosate | + |

Drug combinations of the invention enhance the protective effect of the riluzole toward glutamate toxicity, in the in vitro model, for the three endpoints, with the observation of synergy between the two treatments (Table 4, FIG. 7).

TABLE 4

| Drug Combination | Enhancement of the protective effect of riluzole against glutamate intoxication in the muscle/nerve co-cultures |
|---|---|
| baclofen-cinacalcet-riluzole | + |
| cinacalcet-acamprosate-riluzole | + |
| baclofen-torasemide-riluzole | + |
| baclofen-acamprosate-torasemide-riluzole | + |
| mexiletine-cinacalcet-riluzole | + |
| sulfisoxazole-torasemide-riluzole | + |
| baclofen-acamprosate-riluzole | + |

The inventors have found that combinations of the invention potentiate riluzole protective effect in the muscle/nerve co-culture model. Indeed, baclofen-acamprosate adjunction to the riluzole treated glutamate intoxicated cells results in an improvement of protection afforded to the cells. Moreover, as shown in the FIG. 5, the inventors have been able to identify drug concentrations at which this enhancing effect is particularly important (acamprosate 0.14 nM and baclofen 36 nM). The same is observed for the three endpoints, with other concentrations of riluzole (0.04 and 0.5 µM) and other concentrations of acamprosate and baclofen (0.14 nM and 32 nM, respectively).

As exemplified in FIG. 6, drug combinations of the invention act synergistically with riluzole to protect neuromuscular junctions against glutamate toxicity. Noteworthy, used at a dose barely efficient (36 nM and 0.14 nM of baclofen and acamprosate respectively), the addition of baclofen-acamprosate mix in the culture medium of riluzole treated cells results in almost the doubling (or even more) of the protective effect of riluzole against glutamate injuries.

Switching from riluzole, after the riluzole pre-treatment of 96 hours, toward the combination of acamprosate with baclofen improves the benefit provided by either the riluzole or the baclofen-acamprosate single treatments in the three endpoints of ALS in vitro co-culture model (FIG. 8).

Thus, compositions of the invention are also particularly efficient as adjunctive therapy for other ALS treatments (more particularly, riluzole) or ALS candidate treatments.

3. Combinations Therapies are Efficient in ALS Mouse Model.

Transgenic heterozygous mice B6SJL-Tg(SOD1-G93A) 1Gur/J mice and WT mice (strain 1012, JAX) have been chosen to mimic ALS in this set of experiments. Diseased mice express the SOD1-G93A transgene, designed with a mutant human SOD1 gene (a single amino acid substitution of glycine to alanine at codon 93) driven by its endogenous human SOD1 promoter.

Animals are housed at a standard temperature (22° C.±1° C.) and in a light-controlled environment (lights on from 7 am to 8 pm) with ad libitum access to food and water. Starting at the age of 100 days all G93A SOD1 mice receive wet powdered food (Standard Lab Diet mixed with water to form a paste) and nutritional gel placed in the cage. In addition, water spouts are fitted with extensions to allow mice to easily access from floor level.

Drug Administration

Mice dosed with candidate drug treatment diluted in vehicle from $60^{th}$ day after birth till the mice reach 150 days of age. Diluted solutions of drug candidates are prepared with water at room temperature just before the beginning of the administration. Both riluzole and drug combinations are administrated per os. Cyclodextrin is used as vehicle at the final concentration of 5%, diluted in water at room temperature from stock solution (cyclodextrin 20%). Treatment with drug combinations (10 mL/kg) and vehicle starts at the age of 60 days and continues until the mice reach 150 days of age. Drug combinations were administered per os bis in die (bid) between 8-11 am and 4-7 pm.

Experimental Set Up of Mice

In setting up groups for study (i.e. test or control article treated), transgenic mice are randomized into groups so that whole litters of mice do not end up in a single testing group, thereby avoiding 'litter effects' on the overall results. In addition, the groups are equally balanced for the male/female ratio.

Female mice are housed in groups of 5 maximum and male mice are single housed. Mice are allowed to acclimate to the experimental room for at least one hour prior to the beginning of any experiment. Mice are transported from the colony room to experimental rooms in their home cages.

Body Weight

Weight loss has proven to correlate well with disease development and is easily scored co-jointly with disease stages. The mice will be weighed once-a-week on the same day each week (Mon) at the age of 60-91 days and three times a week (Mon-Wed-Fri) after they reach the age of 91 days (13 weeks).

Clinical Scoring

The original article [45] describing the generation of the SOD1-G93A mice reports an early onset of the disease (ca. 100 days) and a rapid decline with the affected mice reaching the end stage on average within 40 days (typical survival 130-150 days). Hence, the mice are carefully examined using clinical scoring as described below once a week (Mon) until age of 91 days and three times a week (Mon-Wed-Fri) after they reach the age of 91 days.

The earliest clinical signs are tremors and shaking of their limbs when the mice are suspended briefly in the air by their tails. The clinical scoring system is on a scale of 1 to 5; with 1 as the endpoint for euthanasia, and 5 as healthy with little or no signs of onset of disease. Animals are scored by lifting them gently by the base of their tails and observing them for tremors, stiffness and their ability to extend their limbs.

Scoring System:
5=healthy
4-5=mostly healthy, minor tremors, very active, extension of all limbs
4=visible minor tremors, extension of all limbs, very active
3-4=tremors, with some minor stiffness, very active
3=tremors, stiffness of limbs, maybe some minor paralysis, active
2-3=tremors, partial paralysis, stiffness, extension of limbs is labored, active
2=paralysis, somewhat active
1-2=paralysis of hind limbs, no extension of hind limbs, euthanasia may be performed dependent upon the activity of the animal and its ability to right itself within 30 sec
1=endpoint, animal unable to right itself.

The onset of disease is recorded when the score reaches a disease stage of 4.

Behavioral Testing

All behavioral tests are stopped at the age of 20 weeks when approximately 70% of the vehicle group TG mice are lost. After this age the remaining mice are too fragile for motoric testing and are only subjected to body weight measurement, disease stage and survival scoring.

Open Field Test

Open field test measurements are performed before the dosing is started (baseline) and around day 90 (13th age week) and day 110 (16th age week). Mice born within 2-4 days are pooled for open field testing. Activity chambers (Med Associates Inc., St Albans, Vt.; 27×27×20.3 cm) are equipped with IR beams. Mice are placed in the center of the chamber and their behavior is recorded for 10 min. Distance moved, number of vertical rearings and average velocity are recorded.

Rotarod

Rotarod test is performed before the dosing is started (baseline) and around day 90 (13th age week) and day 110 (16th age week): Mice born within 2-4 days are pooled for open field testing. One day session includes a training trial of 5 min at 4 revolutions per minute (RPM) on the rotarod apparatus (AccuScan Instruments, Columbus, USA). One hour later, the animals are tested for 3 consecutive accelerating trials of 6 min with the speed changing from 0 to 40 RPM over 360 sec and an inter-trial interval at least 30 min. The latency to fall from the rod is recorded. Mice remaining on the rod for more than 360 sec are removed and their time scored as 360 sec.

Results

Combinations therapies are efficient in ALS in vivo model.

An improvement of the disease is observed for the diseased animals treated with the drug combinations of the invention. Notably, drug combinations of the invention efficiently improve clinical score of these animals during the different stages of the disease (Table 5) and also performances in the above behavioural tests (Table 6).

TABLE 5

| Drug Combination | Improvement of Global clinical score |
| --- | --- |
| baclofen and cinacalcet | + |
| cinacalcet and acamprosate | + |
| baclofen-torasemide | + |
| baclofen-acamprosate-torasemide | + |
| mexiletine and cinacalcet | + |
| sulfisoxazole and torasemide | + |
| baclofen and acamprosate | + |

TABLE 6

| | Behavioral testing Improvement of performances | |
| --- | --- | --- |
| Drug Combination | rotarod test | open field test |
| baclofen and cinacalcet | + | + |
| cinacalcet and acamprosate | + | + |
| baclofen-torasemide | + | + |
| baclofen-acamprosate-torasemide | + | + |
| mexiletine and cinacalcet | + | + |
| sulfisoxazole and torasemide | + | + |
| baclofen and acamprosate | + | + |

The compositions of the invention are also efficient in improving clinical score and course of the disease in riluzole treated animals (Table 7).

TABLE 7

| Drug Combination | Improvement of Global clinical score in riluzole treated animals |
|---|---|
| baclofen and cinacalcet | + |
| cinacalcet and acamprosate | + |
| baclofen-torasemide | + |
| baclofen-acamprosate-torasemide | + |
| mexiletine and cinacalcet | + |
| sulfisoxazole and torasemide | + |
| baclofen and acamprosate | + |

REFERENCES

1 Camu W, Khoris J, Moulard B, Salachas F, Briolotti V, Rouleau G A & Meininger V (1999) Genetics of familial ALS and consequences for diagnosis. French ALS Research Group. *J. Neurol. Sci.* 165 Suppl, S21-6.
2 Mitchell J D & Borasio G D (2007) Amyotrophic lateral sclerosis. *Lancet* 369, 2031-41.
3 Phukan J, Pender N P & Hardiman O (2007) Cognitive impairment in amyotrophic lateral sclerosis. *Lancet. Neurol.* 6, 994-1003.
4 Hammad M, Silva A, Glass J, Sladky J T & Benatar M (2007) Clinical, electrophysiologic, and pathologic evidence for sensory abnormalities in ALS. *Neurology* 69, 2236-42.
5 Bigio E H, Lipton A M, White C L, Dickson D W & Hirano A (2003) Frontotemporal and motor neurone degeneration with neurofilament inclusion bodies: additional evidence for overlap between FTD and ALS. *Neuropathol. Appl. Neurobiol.* 29, 239-53.
6 Yoshida S, Kihira T & Yase Y (2007) [Etiology of Kii ALS/PDC, featuring a mineral hypothesis]. *Rinsho Shinkeigaku* 47, 970-3.
7 Waring S C, Esteban-Santillan C, Reed D M, Craig U-K, Labarthe D R, Petersen R C & Kurland L T Incidence of amyotrophic lateral sclerosis and of the parkinsonism-dementia complex of Guam, 1950-1989. *Neuroepidemiology* 23, 192-200.
8 Sapp P C, Rosen D R, Hosler B A, Esteban J, McKenna-Yasek D, O'Regan J P, Horvitz H R & Brown R H (1995) Identification of three novel mutations in the gene for Cu/Zn superoxide dismutase in patients with familial amyotrophic lateral sclerosis. *Neuromuscul. Disord.* 5, 353-7.
9 Hentati A, Ouahchi K, Pericak-Vance M A, Nijhawan D, Ahmad A, Yang Y, Rimmler J, Hung W, Schlotter B, Ahmed A, Ben Hamida M, Hentati F & Siddique T (1998) Linkage of a commoner form of recessive amyotrophic lateral sclerosis to chromosome 15q15-q22 markers. *Neurogenetics* 2, 55-60.
10 Ruddy D M, Parton M J, Al-Chalabi A, Lewis C M, Vance C, Smith B N, Leigh P N, Powell J F, Siddique T, Meyjes E P, Baas F, de Jong V & Shaw C E (2003) Two families with familial amyotrophic lateral sclerosis are linked to a novel locus on chromosome 16q. *Am. J. Hum. Genet.* 73, 390-6.
11 Pasinelli P & Brown R H (2006) Molecular biology of amyotrophic lateral sclerosis: insights from genetics. *Nat. Rev. Neurosci.* 7, 710-23.
12 Gurney M E (1994) Transgenic-mouse model of amyotrophic lateral sclerosis. *N. Engl. J. Med.* 331, 1721-2.
13 Deng H-X, Shi Y, Furukawa Y, Zhai H, Fu R, Liu E, Gorrie G H, Khan M S, Hung W-Y, Bigio E H, Lukas T, Dal Canto M C, O'Halloran T V & Siddique T (2006) Conversion to the amyotrophic lateral sclerosis phenotype is associated with intermolecular linked insoluble aggregates of SOD1 in mitochondria. *Proc. Natl. Acad. Sci. U.S.A.* 103, 7142-7.
14 Cai H, Lin X, Xie C, Laird F M, Lai C, Wen H, Chiang H-C, Shim H, Farah M H, Hoke A, Price D L & Wong P C (2005) Loss of ALS2 function is insufficient to trigger motor neuron degeneration in knock-out mice but predisposes neurons to oxidative stress. *J. Neurosci.* 25, 7567-74.
15 Comi G P, Bordoni A, Salani S, Franceschina L, Sciacco M, Prelle A, Fortunato F, Zeviani M, Napoli L, Bresolin N, Moggio M, Ausenda C D, Taanman J W & Scarlato G (1998) Cytochrome c oxidase subunit I microdeletion in a patient with motor neuron disease. *Ann. Neurol.* 43, 110-6.
16 Borthwick G M, Taylor R W, Walls T J, Tonska K, Taylor G A, Shaw P J, Ince P G & Turnbull D M (2006) Motor neuron disease in a patient with a mitochondrial tRNAIle mutation. *Ann. Neurol.* 59, 570-4.
17 Lambrechts D, Storkebaum E, Morimoto M, Del-Favero J, Desmet F, Marklund S L, Wyns S, Thijs V, Andersson J, van Marion I, Al-Chalabi A, Bornes S, Musson R, Hansen V, Beckman L, Adolfsson R, Pall H S, Prats H, Vermeire S, Rutgeerts P, Katayama S, Awata T, Leigh N, Lang-Lazdunski L, Dewerchin M, Shaw C, Moons L, Vlietinck R, Morrison K E, Robberecht W, Van Broeckhoven C, Collen D, Andersen P M & Carmeliet P (2003) VEGF is a modifier of amyotrophic lateral sclerosis in mice and humans and protects motoneurons against ischemic death. *Nat. Genet.* 34, 383-94.
18 Lacomblez L, Bensimon G, Leigh P N, Guillet P & Meininger V (1996) Dose-ranging study of riluzole in amyotrophic lateral sclerosis. Amyotrophic Lateral Sclerosis/Riluzole Study Group II. *Lancet* 347, 1425-31.
19 Ettmayer P, Amidon G L, Clement B & Testa B (2004) Lessons learned from marketed and investigational prodrugs. *J. Med. Chem.* 47, 2393-404.
20 Beaumont K, Webster R, Gardner I & Dack K (2003) Design of ester prodrugs to enhance oral absorption of poorly permeable compounds: challenges to the discovery scientist. *Curr. Drug Metab.* 4, 461-85.
21 Yang C Y, Dantzig A H & Pidgeon C (1999) Intestinal peptide transport systems and oral drug availability. *Pharm. Res.* 16, 1331-43.
22 Steffansen B, Nielsen C U, Brodin B, Eriksson A H, Andersen R & Frokjaer S (2004) Intestinal solute carriers: an overview of trends and strategies for improving oral drug absorption. *Eur. J. Pharm. Sci.* 21, 3-16.
23 Heimbach T, Oh D M, Li L Y, Rodriguez-Hornedo N, Garcia G & Fleisher D (2003) Enzyme-mediated precipitation of parent drugs from their phosphate prodrugs. *Int. J. Pharm.* 261, 81-92.
24 Stella V J (2007) *Prodrugs: challenges and rewards.* (A. Press and Springer, eds.) Springer Singapore Pte. Limited, New-York.
25 Wermuth C G (2003) Designing prodrugs and biopre-cusrors. In *The Practice of Medicinal Chemistry* (Hardbound, ed), 2nd ed., pp. 561-585. Academic Press.
26 Pezron I, Mitra A K, Duvvuri S & Tirucherai G S (2002) Prodrug strategies in nasal drug delivery. *Expert Opin. Ther. Pat.* 12, 331-340.
27 Stella V J (2004) Prodrugs as therapeutics. *Expert Opin. Ther. Pat.* 14, 277-280.
28 Higuchi T & Stella V J (1975) *Pro-drugs as Novel Drug Delivery System*, ACS Sympos American Chemical Society, Washington, D.C.

29 Roche E B (1977) *Design of biopharmaceutical properties through prodrugs and analogs: a symposium*, American P The Academy, Washington, D.C.

30 Stella V J & Nti-Addae K W (2007) Prodrug strategies to overcome poor water solubility. *Adv. Drug Deliv. Rev.* 59, 677-94.

31 Lal R, Sukbuntherng J, Tai E H L, Upadhyay S, Yao F, Warren M S, Luo W, Bu L, Nguyen S, Zamora J, Peng G, Dias T, Bao Y, Ludwikow M, Phan T, Scheuerman R A, Yan H, Gao M, Wu Q Q, Annamalai T, Raillard S P, Koller K, Gallop M A & Cundy K C (2009) Arbaclofen placarbil, a novel R-baclofen prodrug: improved absorption, distribution, metabolism, and elimination properties compared with R-baclofen. *J. Pharmacol. Exp. Ther.* 330, 911-21.

32 Xu F, Peng G, Phan T, Dilip U, Chen J L, Chernov-Rogan T, Zhang X, Grindstaff K, Annamalai T, Koller K, Gallop M A & Wustrow D J (2011) Discovery of a novel potent GABA(B) receptor agonist. *Bioorg. Med. Chem. Lett.* 21, 6582-5.

33 Hanafi R, Mosad S, Abouzid K, Niess R & Spahn-Langguth H (2011) Baclofen ester and carbamate prodrug candidates: a simultaneous chromatographic assay, resolution optimized with DryLab. *J. Pharm. Biomed. Anal.* 56, 569-76.

34 Leach A R & Gillet V J *An Introduction to Chemoinformatics* (Springer-Verlag New York Inc, ed.).

35 Rahman S A, Bashton M, Holliday G L, Schrader R & Thornton J M (2009) Small Molecule Subgraph Detector (SMSD) toolkit. *J. Cheminform.* 1, 12.

36 Wishart D S, Knox C, Guo A C, Cheng D, Shrivastava S, Tzur D, Gautam B & Hassanali M (2008) DrugBank: a knowledgebase for drugs, drug actions and drug targets. *Nucleic Acids Res.* 36, D901-6.

37 Stahl H & Wermuth C G (2011) *Pharmaceutical salts: Properties, selection, and use*, 2nd ed. (Wiley-VCH, ed.).

38 Gennaro A R (2000) *Remington: The Science and Practice of Pharmacy*, 20th ed. (A. D. Gennaro, W. Lippincott, and Wilkins, eds.) Lippincott Williams & Wilkins.

39 Swarbrick J & Boylan J C (eds.) *Encyclopedia of Pharmaceutical Technology* Dekker, Marcel, New-York.

40 Slinker B K (1998) The Statistics of Synergism. *J. Mol. Cell. Cardiol.* 30, 723-731.

41 LOEWE S (1953) The problem of synergism and antagonism of combined drugs. *Arzneimittelforschung.* 3, 285-90.

42 Grabovsky Y & Tallarida R J (2004) Isobolographic analysis for combinations of a full and partial agonist: curved isoboles. *J. Pharmacol. Exp. Ther.* 310, 981-6.

43 Singer C A, Figueroa-Masot X A, Batchelor R H & Dorsa D M (1999) The mitogen-activated protein kinase pathway mediates estrogen neuroprotection after glutamate toxicity in primary cortical neurons. *J. Neurosci.* 19, 2455-63.

44 Braun S, Croizat B, Lagrange M C, Warter J M & Poindron P (1996) Neurotrophins increase motoneurons' ability to innervate skeletal muscle fibers in rat spinal cord—human muscle cocultures. *J. Neurol. Sci.* 136, 17-23.

45 Gurney M E, Pu H, Chiu A Y, Dal Canto M C, Polchow C Y, Alexander D D, Caliendo J, Hentati A, Kwon Y W & Deng H X (1994) Motor neuron degeneration in mice that express a human Cu,Zn superoxide dismutase mutation. *Science* 264, 1772-5.

We claim:

1. A method of treating amyotrophic lateral sclerosis (ALS) or a related motor neuron disorder selected from the group consisting of primary lateral sclerosis, progressive muscular atrophy, pseudobulbar palsy and progressive bulbar palsy in a subject suffering therefrom, the method comprising administering to the subject an effective amount of a compound selected from sulfisoxazole or torasemide, or salts, or prodrugs, or sustained-release formulations thereof, in combination with at least one second different compound selected from sulfisoxazole, torasemide or riluzole, or salts, or prodrugs, or sustained-release formulations thereof.

2. The method of claim 1, wherein the treatment of ALS or a related motor neuron disorder reduces motor neuron degeneration in said subject.

3. The method of claim 1, comprising administering one of the following combinations of compounds:
    torasemide and sulfisoxazole,
    torasemide and riluzole,
    sulfisoxazole and riluzole, or
    torasemide, sulfisoxazole and riluzole,
or salts, or prodrugs, or sustained-release formulations of each of said compounds.

4. The method of claim 1, wherein the compounds are administered with a pharmaceutically acceptable carrier or excipient.

5. The method of claim 1, wherein the compounds are administered repeatedly to the subject.

6. The method of claim 1, wherein the compounds are formulated or administered together, separately or sequentially.

7. The method of claim 6, wherein the compounds are formulated together.

8. The method of claim 3, wherein, when riluzole, or a salt, prodrug, or sustained-release formulation thereof, is present in the combination of compounds, it is administered alternately with the sulfisoxazole or torasemide, or the combination thereof, or the salts, or prodrugs, or sustained-release formulations thereof.

9. The method of claim 1, wherein, when sulfisoxazole is present in the combination of compounds, it is administered in a dosage of less than 800 mg per day.

10. The method of claim 1, wherein, when torasemide is present in the combination of compounds, it is administered in a dosage from about 0.05 to 4 mg per day.

11. The method of claim 1, wherein, when riluzole is present in the combination of compounds, it is administered in a dosage from about 0.01 to 50 mg per day.

12. The method of claim 1, wherein said compounds are administered orally.

13. A pharmaceutical composition comprising one of the following combinations of compounds:
    torasemide and sulfisoxazole,
    torasemide and riluzole,
    sulfisoxazole and riluzole, or
    torasemide, sulfisoxazole and riluzole,
or salts, or prodrugs, or sustained-release formulations of each of said compounds.

14. A method for protecting neuromuscular junctions against glutamate toxicity in a subject in need thereof, comprising administering to the subject an effective amount of a compound selected from sulfisoxazole or torasemide, or salts, or prodrugs, or sustained-release formulations thereof, in combination with at least one second different compound selected from sulfisoxazole, torasemide or riluzole, or salts, or prodrugs, or sustained-release formulations thereof.

15. A method in accordance with claim 14, comprising administering one of the following combinations of compounds:
    torasemide and sulfisoxazole,
    torasemide and riluzole, sulfisoxazole and riluzole, or
torasemide, sulfisoxazole and riluzole,
or salts, or prodrugs, or sustained-release formulations of each of said compounds.

\* \* \* \* \*